United States Patent
Cui et al.

(10) Patent No.: US 10,294,242 B2
(45) Date of Patent: May 21, 2019

(54) DIARYL MACROCYCLE POLYMORPH

(71) Applicant: TP THERAPEUTICS, INC., San Diego, CA (US)

(72) Inventors: Jingrong J. Cui, San Diego, CA (US); Evan W. Rogers, San Diego, CA (US)

(73) Assignee: TP Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/741,893

(22) PCT Filed: Jul. 5, 2016

(86) PCT No.: PCT/US2016/040972
§ 371 (c)(1),
(2) Date: Jan. 4, 2018

(87) PCT Pub. No.: WO2017/007759
PCT Pub. Date: Jan. 12, 2017

(65) Prior Publication Data
US 2018/0194777 A1    Jul. 12, 2018

Related U.S. Application Data

(60) Provisional application No. 62/218,672, filed on Sep. 15, 2015, provisional application No. 62/188,846, filed on Jul. 6, 2015.

(51) Int. Cl.
*C07D 498/18* (2006.01)
*C07C 271/16* (2006.01)
*A61P 35/00* (2006.01)

(52) U.S. Cl.
CPC ............ *C07D 498/18* (2013.01); *A61P 35/00* (2018.01); *C07C 271/16* (2013.01); *C07B 2200/07* (2013.01); *C07B 2200/13* (2013.01)

(58) Field of Classification Search
CPC .................................................. C07D 498/18
See application file for complete search history.

(56) References Cited

U.S. PATENT DOCUMENTS

| | | |
|---|---|---|
| 8,680,111 B2 | 3/2014 | Bailey et al. |
| 8,815,872 B2 | 8/2014 | Yu et al. |
| 8,933,084 B2 | 1/2015 | Andrews et al. |
| 9,714,258 B2 | 7/2017 | Cui et al. |
| 2011/0294801 A1 | 12/2011 | Yu et al. |
| 2013/0203776 A1 | 8/2013 | Andrews et al. |
| 2013/0245021 A1 | 9/2013 | Bi et al. |
| 2013/0252961 A1 | 9/2013 | Bailey et al. |
| 2014/0107099 A1 | 4/2014 | Blaney et al. |
| 2014/0206605 A1 | 7/2014 | Beutner et al. |

FOREIGN PATENT DOCUMENTS

| | | |
|---|---|---|
| JP | 2012-502043 | 1/2012 |
| WO | 2010/028116 | 3/2010 |
| WO | 2010033941 | 3/2010 |
| WO | 2010048314 | 4/2010 |
| WO | 2010051549 | 5/2010 |
| WO | 2011/146336 | 11/2011 |
| WO | 2012034091 | 3/2012 |
| WO | 2012/136859 | 10/2012 |
| WO | 2013/001310 | 1/2013 |
| WO | 2013028465 | 2/2013 |
| WO | 2013045653 | 4/2013 |
| WO | 2013/134219 | 9/2013 |
| WO | 2013134228 | 9/2013 |
| WO | 2013147711 | 10/2013 |
| WO | 2015/112806 | 7/2015 |
| WO | WO2015112806 | 7/2015 |

OTHER PUBLICATIONS

Miller et. al. "Solvent Systems for Crystallization and Polymorph Selection" Chapter 3 in Solvent Systems and Their Selection in Pharmaceutics and Biopharmaceutics Series Biotechnology: Pharmaceutical Aspects vol. VI Augustijns, Patrick; Brewster, Marcus (Eds.) 2007.*
Matthew L. Peterson et. al. "Expanding the Scope of Crystal Form Evaluation in Pharmaceutical Science" Journal of Pharmacy & Pharmaceutical Science 2006 (9(3):317-326.*
Manning, G. et al., *Science* 2002, 298, 1912-1934.
Sawyers, C., *Nature* 2004, 432, 294-297.
Park, M. et al., *Cell* 1986, 45, 895-904.
Bottaro, D. P. et al., *Science* 1991, 251, 802-804.
Trusolino, L. et al., *Nature Rev. Mol. Cell Biol.* 2010, 11, 834-848.
Gherardi, E. et al., *Nature Rev. Cancer* 2012, 12, 89-103.
Engelman, J. A. et al., *Science* 2007, 316, 1039-1043.
Wilson, T.R. et al., *Nature* 2012, 487, 505-509.
Pulford, K. et al., *Cell Mol. Life Sci.* 2004, 61, 2939.
Morris, S.W. et al., *Science* 1994, 263, 1281.
Bischof, D. et al., *Mol. Cell Biol.*, 1997, 17, 2312-2325.
Soda, M. et al., *Nature* 2007, 448, 561-566.
Mossé, Y. P. et al., *Nature* 2008, 455, 930-935.
Thiele, C. J. et al., *Clin. Cancer Res.* 2009, 15, 5962-5967.
Pierotti, M. A. et al., *Cancer Lett.* 2006, 232, 90-98.
Vaishnavi, A. et al., *Nat. Med.* 2013, 19, 1469-1472.
Verma, A. et al., *Mol. Cancer Ther.* 2011, 10, 1763-1773.
Zhang, Z. et al., *Nat. Genet.* 2012, 44, 852-860.
Cui, J. J. et al., *J. Med. Chem.* 2011, 54, 6342-6363.
Katayama, R. et al., *Sci. Transl. Med.* 2012, 4, 120ra17.
Quintas-Cardama, A. et al., *Nat. Rev. Drug Discov.* 2011, 10(2), 127-40.
Pesu, M. et al., *Immunol. Rev.* 2008, 223, 132-142.
Murray, P.J., *J. Immunol.* 2007, 178(5), 2623-2329.
Muller, M. et al., *Nature* 1993, 366(6451), 129-135.
Neubauer, H. et al., *Cell* 1998 93(3), 397-409.
Nosaka, T. et al., *Science* 1995, 270(5237), 800-802.

(Continued)

*Primary Examiner* — David K O'Dell
(74) *Attorney, Agent, or Firm* — Barnes & Thornburg, LLP

(57) ABSTRACT

This disclosure relates to polymorphs of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one that are useful in the treatment of disease, such as cancer, in mammals. This disclosure also relates to compositions including such polymorphs, and to methods of using such compositions in the treatment of diseases, such as cancer, in mammals, especially in humans.

20 Claims, 2 Drawing Sheets

(56) References Cited

OTHER PUBLICATIONS

Vainchenker, W. et al., *Semin. Cell. Dev. Biol.* 2008, 19(4), 385-393.
Levine, R.L. et al., *Cancer Cell* 2005, 7(4), 387-397.
Kralovics, R. et al., *N. Engl. J. Med.* 2005, 253(17), 1779-1790.
James, C. et al., *Nature* 2005, 434(7037), 1144-1148.
Baxter, E.J. et al. *Lancet* 2005, 365(9464), 1054-1061.
Sonbol, M.B. et al., *Ther. Adv. Hematol.* 2013, 4(1), 15-35.
LaFave, L.M. et al., *Trends Pharmacol. Sci.* 2012, 33(11), 574-582.
Verstovsek, S. et al., *N. Engl. J. Med.* 2012, 366(9), 799-807.
Quintas-Cardama, A. et al., *Blood* 2010, 115(15), 3109-3117.
Nefedova, Y. et al., Cancer Res 2005; 65(20): 9525-35.
Davies, K. D. et al., Clin Cancer Res 2013, 19 (15): 4040-4045.
Awad, M. M. et al., N Engl J Med. 2013, 368(25):2396-2401.
Charest A, et al *Genes Chromosomes Cancer* 2003, 37, 58.
Takeuchi K, et al *Nat. Med.* 2012, 18, 378.
Gu TL, et al *PLoS One*. 2011, 6, e15640.
Lacronique V, et al. *Science* 1997, 278, 5341, 1309-12.
Reiter A, et al. *Cancer Res*. 2005, 65, 7, 2662-7.
Zhang S, et al Trends Pharmacol Sci. 2012, 33, 122.
Bromann PA, Oncogene 2004, 23, 7957-7968.
Golubovskaya VM, *Front Biosci* (Landmark Ed). 2014; 19: 687-706.
Liu L, et al. Nature, 2012, 483, 608-612.
Summy JM, et al. *Cancer Metastasis Rev*. 2003, 22, 337-358.
Scancier F. et al. *PLoS One*. 2011, 6(2): e17237.
Ongusaha PP, et al. *EMBO J*. 2003, 22, 1289-1301.
Hammerman PS, et al. Cancer Discov. 2011, 1, 78-89.
Tomasson MH, et al, *Blood* 2008, 111 :4797-4808.
Yu J. et al., *Cancer Cell*, 2010, 17, 5, 443-54.
Advani, A.S. et al. *Leukemia Research*, 2002, 26, 8, 713-720.
Gottesman, M.M., *Annu. Rev. Med.*, 2002, 53, 615-627.
Anastassiadis T, et al *Nat Biotechnol*. 2011, 29, 1039.
Vetrie D. et al. *Nature* 1993, 361, 226-233.
Mohamed AJ et al, *Immunological Reviews*, 2009, 228, 58-73.
Grande, E. et al., *Mol. Cancer Ther*. 2011, 10, 569-579.
Monti, E. 2007. Molecular Determinants of Intrinsic Multidrug Resistance in Cancer Cells and Tumors in B. Teicher (Ed.), *Cancer Drug Resistance* (pp. 241-260).
International Search Report and Written Opinion prepared for PCT/US2016/043132, dated Sep. 28, 2016, 8 pages.
International Search Report and Written Opinion prepared for PCT/US2016/040329, dated Sep. 7, 2016, 13 pages.
International Search Report and Written Opinion prepared for PCT/US2016/040972, dated Sep. 13, 2016, 8 pages.
PCT Search Report and Written Opinion for PCT/US2015/012597, dated Aug. 28, 2015.
McCarthy et al. "Tropomyosin receptor kinase inhibitors: a patent update 2009-2013," Expert Opinions 2014, pp. 731-744.
International Search Report and Written Opinion prepared for PCT/US2017/044214, dated Dec. 1, 2017, 11 pages.
Couronne L, et al. Blood 2013, 122, 811.
Di Paolo JA, et al. Nature Chemical Biology 2011, 7, 41-50.
Schiller J H et al., N Engl J Med, 346: 92-98, 2002.
Takahashi, M. et al. Cell. 1985, 42:581-588.
Pachnis, V., et al. Development 1993, 119, 1005-1017.
Schuchardt, A. et al. Nature 1994, 367:380-383.
Grieco, M. et al. Cell. 1990, 23; 60 (4):557-63.
Gainor JF, Shaw AT. Oncologist. 2013, 18(7):865-75.
Liu Z, et al. J. Clin. Endocrinol. Metab. 2004, 89, 3503-3509.
Cooper, C. S., et al Molecular cloning of a new transforming gene from a chemically transformed human cell line. Nature 1984, 311, 29-33.
Boccaccio, C.; Comoglio, P. M. Invasive growth: a MET-driven generic programme for cancer and stem cells. Nat. Rev. Cancer 2006, 6, 637-645.

Ma, PC et al. Expression and mutational analysis of MET in human solid cancers. Genes Chromosomes Cancer 2008, 47, 1025-1037.
Maulik, G., et al. Role of the hepatocyte growth factor receptor, MET, in oncogenesis and potential for therapeutic inhibition. Cytokine Growth Factor Rev. 2002, 13, 41-59.
Smolen, G. A., et al. Amplification of MET may identify a subset of cancers with extreme sensitivity to the selective tyrosine kinase inhibitor PHA-665752. Proc. Natl. Acad. Sci. U. S. A. 2006, 103, 2316-2321.
Ghiso, E.; Giordano, S. Targeting MET: why, where and how? Curr. Opin. Pharmacol. 2013, 13, 511-518.
Otsuka, T., et al. MET autocrine activation induces development of malignant melanoma and acquisition of the metastatic phenotype. Cancer Res. 1998, 58, 5157-5167.
Xie, Q., et al. Hepatocyte growth factor (HGF) autocrine activation predicts sensitivity to MET inhibition in glioblastoma. Proc. Natl. Acad. Sci. U. S. A. 2012, 109, 570-575.
Kentsis, A., et al. Autocrine activation of the MET receptor tyrosine kinase in acute myeloid leukemia. Nat. Med. 2012, 18, 1118-1122.
Yu, Helena A., et al. Analysis of tumor specimens at the time of acquired resistance to EGFR-TKI therapy in 155 patients with EGFR-mutant lung cancers. Clin. Cancer Res. 2013, 19, 2240-2247.
Yano, S., et al. Hepatocyte growth factor induces gefitinib resistance of lung adenocarcinoma with epidermal growth factor receptor-activating mutations. Cancer Res. 2008, 68, 9479-9487.
Bardelli, A., et al. Amplification of the MET Receptor Drives Resistance to Anti-EGFR Therapies in Colorectal Cancer. Cancer Discov. 2013, 3, 658-673.
Straussman, R., et al. Tumour micro-environment elicits innate resistance to RAF inhibitors through HGF secretion. Nature 2012, 487, 500-504.
Harbinski, F., et al. Rescue screens with secreted proteins reveal compensatory potential of receptor tyrosine kinases in driving cancer growth. Cancer Discov. 2012, 2, 948-959.
Parsons, S. J., et al. Src family kinases, key regulators of signal transduction. Oncogene. 2004, 23, 7906-7909.
Wojcik, E. J., et al. A novel activating function of SRC and STAT3 on HGF transcription in mammary carcinoma cells. Oncogene. 2006, 25, 2773-84.
Dulak AM, et al. HGF-independent potentiation of EGFR action by MET. Oncogene. 2011, 30, 3625-3635.
Stabile, L. P., et al. c-SRC activation mediates erlotinib resistance in head and neck cancer by stimulating MET. Clin Cancer Res. 2012, 19, 1-13.
Sen, B., et al. Distinct interactions between SRC and MET in mediating resistance to SRC inhibition in head and neck cancer. Clin Cancer Res. 2010, 17, 1-11.
Bertotti, A., et al. Inhibition of SRC impairs the growth of MET-addicted gastric tumors. Clin Cancer Res. 2010, 16, 3933-3943.
Wrobel CN, et al. Autocrine CSF1R activation promotes SRC-dependent disruption of mammary epithelial architecture. J Cell Biol. 2004, 165, 263-273.
Ravi V, et al. Treatment of tenosynovial giant cell tumor and pigmented villonodular synovitis. Curr Opin Oncol. 2011, 23, 361-366.
Gridelli, C. et al., *Cancer Treat Rev*. 2014, 40, 300-306.
Toso, A. et al., Cell Reports 2014, 9, 75-89.
Shaw, A. T. et al., N Engl J Med. 2014, 371(21):1963-1971.
Politi K, Clin Cancer Res. 2014, 20, 5576.
Crystal AS, Science. 2014, 346, 1480.
Vaishnavi A, et al Cancer Discov. 2015, 5, 25.
Park, K-S, et al. J Clin Invest. 2014, 124(7):3003-3015.
Shi L, et al. Br J Cancer. 2014, 111(12):2316-27.
Stransky N, et al. Nature Communications 2014, 5, 4846.
Schwarz LJ, et al. J Clin Invest. 2014, 124, 5490-5502.
Zardan A., et al. Oncogenesis 2014, 3, e115.
Rudd ML, et al. BMC Cancer 2014, 14, 884.
Furman RR, et al. New England Journal of Medicine, 2014, 370, 2352-2354.
Chiron D, et al. Cancer Discovery, 2014, 4, 1022-1035.
Woyach JA, et al. New England Journal of Medicine, 2014, 370, 2286-2294.

(56) References Cited

OTHER PUBLICATIONS

Mulligan, LM. Nat Rev Cancer. 2014, 14(3):173-86.
Fujita-Sato, S., et al. Enhanced MET Translation and Signaling Sustains K-Ras-Driven Proliferation under Anchorage-Independent Growth Conditions. Cancer Res. 2015, 75, 2851-2862.
Song N, et al. Cetuximab-induced MET activation acts as a novel resistance mechanism in colon cancer cells. Int J Mol Sci. 2014, 15, 5838-5851.
Ries CH, et al. Targeting tumor-associated macrophages with anti-CSF1R antibody reveals a strategy for cancer therapy. Cancer Cell. 2014, 25, 846-859.
Baldanzi et al., "Physiological Signaling and Structure of the HGF Receptor MET", Biomedicines 2015, 3, 1-31. First published Dec. 31, 2014.
Gargalionis et al., "The molecular rationale of Src inhibition in colorectal carcinomas", Int. J. Cancer: 134, 2019-2029 (2014). Published online Jun. 21, 2013.
Heynen et al., "Resistance to targeted cancer drugs through hepatocyte growth factor signaling", Cell Cycle, 2014, 13:24, 3808-3817. Accepted Nov. 11, 2014.
Okamoto et al., "Identification of c-Src as a Potential Therapeutic Target for Gastric Cancer and of MET Activation as a Cause of Resistance to c-Src Inhibition", Mol Cancer Ther., May 2010; 9(5): 1188-97. Published online Apr. 20, 2010,
Pennacchietti et al., "Microenvironment-Derived HGF Overcomes Genetically Determined Sensitivity to Anti-MET Drugs", Cancer Res. Nov. 15, 2014; 74(22): 6598-609. Published online Sep. 12, 2014.
Vergani et al., "Identification of MET and SRC Activation in Melanoma Cell Lines Showing Primary Resistance to PLX4032", Neoplasia. Dec. 2011; 13(12): 1132-42.
PCT Search Report and Written Opinion for PCT/US2016/040972, dated Aug. 18, 2016.
Pachter et al., "The Chemistry of Hortiamine and 6-Methoxyrhetsinine," J. Am. Chem. Soc., 1961, 83, 635-642.
Kiselyov, Alexander S., "Solid support synthesis of 15-membered macrocycles containing a serotonin unit," Tetrahedron Letters 46 (2005) 3007-3010.
Halland et al. "Small Macrocycles as Highly Active Integrin α2β1 Antagonists," ACS Medicinal Chemistry Letters, Jan. 10, 2014, 5, 193-198.
Lim et al., "Discovery of 5-Amino-N-(1H-pyrazol-4-yl)pyrazolo[1,5-a]pyrimidine-3-carboxamide Inhibitors of IRAK4," ACS Medicinal Chemistry Letters (2015), 6(6), 683-688.

* cited by examiner

DIARYL MACROCYCLE POLYMORPH

CROSS-REFERENCE TO RELATED APPLICATIONS

This application is a national stage entry under 35 USC § 371 of PCT International Application Number PCT/US2016/040972, filed Jul. 5, 2016, which claims the benefit of U.S. Provisional Patent Application Ser. No. 62/188,846, filed Jul. 6, 2015, and U.S. Provisional Patent Application Ser. No. 62/218,672, filed on Sep. 15, 2015, the disclosures of which are incorporated herein by reference.

TECHNICAL FIELD

This disclosure relates to polymorphs of (7S,13R)-11-fluoro-7,13-dimethyl-6,7,13,14-tetrahydro-1,15-ethenopyrazolo[4,3-][1,4,8,10]benzoxatriazacyclotridecin-4(5H)-one that are useful in the treatment of disease, such as cancer, in mammals. This disclosure also relates to compositions including such polymorphs, and to methods of using such compositions in the treatment of diseases, such as cancer, in mammals, especially in humans.

BACKGROUND

The compound (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (also herein referred to as "Compound I") represented by the formula I

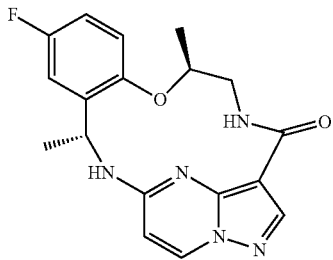

is a potent small-molecule multi-target kinase inhibitor showing activity against wild-type and mutant ALK (anaplastic lymphoma kinase), wild-type and mutant ROS1 (ROS1 proto-oncogene receptor tyrosine kinase), the TRK family of kinases (tropomyosin-related receptor tyrosine kinases), JAK2 of the Janus family of kinases, SRC (Src family of protein tyrosine kinases (SFKs)) and FAK (focal adhesion kinase). Compound I has properties, including anti-tumor properties, that are pharmacologically mediated through inhibition of tyrosine kinase receptors. Compound I is disclosed in International Patent Application No. PCT/US2015/012597, which is incorporated herein by reference in its entirety.

Protein kinases are key regulators for cell growth, proliferation and survival. A variety of diseases, such as cancer, pain, neurological diseases, autoimmune diseases, and inflammation, have been shown to be mediated by receptor tyrosine kinases, such as ALK, ROS1, TRK, JAK2, SRC and FAK. For example, genetic and epigenetic alterations can accumulate in cancer cells leading to abnormal activation of signal transduction pathways which drive malignant processes. Manning, G. et al., *Science* 2002, 298, 1912-1934. Pharmacological inhibition of these signaling pathways presents promising intervention opportunities for targeted cancer therapies. Sawyers, C., *Nature* 2004, 432, 294-297.

While Compound I has found application in treating disease associated with receptor tyrosine kinases, such as ALK, ROS1, TRK, JAK2, SRC and FAK, it is advantageous to have polymorphic forms having improved properties, such as improved crystallinity, dissolution properties, and/or decreased hygroscopicity, while maintaining chemical and enantiomeric stability properties.

SUMMARY

In one aspect, the present disclosure provides a crystalline form of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one.

In another embodiment, the crystalline polymorph form of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one is anhydrous.

In another embodiment, the crystalline polymorph form 1 of compound I can be represented by the formula

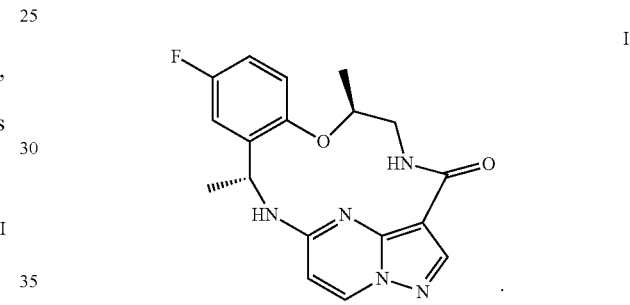

In a further embodiment, the crystalline polymorph form has a powder X-ray diffraction pattern comprising a peak at diffraction angle (2θ) of 27.4±0.1. In a further embodiment, the crystalline polymorph form has a powder X-ray diffraction pattern comprising peaks at diffraction angles (2θ) of 9.4±0.1 and 27.4±0.1. In a further embodiment, the crystalline polymorph form has a powder X-ray diffraction pattern comprising peaks at diffraction angles (2θ) of 9.4±0.1, 18.8±0.1, and 27.4±0.1. In a further embodiment, the crystalline polymorph form has a powder X-ray diffraction pattern comprising peaks at diffraction angles (2θ) of 9.4±0.1, 16.5±0.1, 18.8±0.1, and 27.4±0.1. In a further embodiment, the crystalline polymorph form has a powder X-ray diffraction pattern comprising peaks at diffraction angles (2θ) of 9.4±0.1, 16.5±0.1, 18.8±0.1, 22.8±0.1, and 27.4±0.1. In a further embodiment, the crystalline polymorph form has a powder X-ray diffraction pattern comprising peaks at diffraction angles (2θ) of 9.4±0.1, 16.1±0.1, 16.5±0.1, 18.8±0.1, 22.8±0.1, and 27.4±0.1. In a further embodiment, the crystalline polymorph form has a powder X-ray diffraction pattern comprising peaks at diffraction angles (2θ) of 9.4±0.1, 16.1±0.1, 16.5±0.1, 18.8±0.1, 21.2±0.1, 22.8±0.1, and 27.4±0.1.

In a further aspect the crystalline form has a powder X-ray diffraction pattern comprising peaks at diffraction angles (2θ) essentially the same as shown in FIG. 1.

The present disclosure further provides a pharmaceutical composition comprising a polymorph form 1 of Compound I of the formula

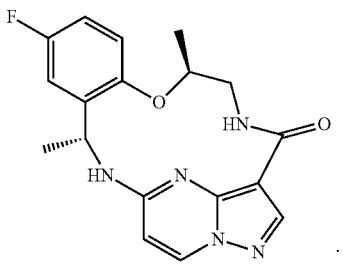

I

The present disclosure further provides a capsule comprising pharmaceutical compositions as described herein.

In another aspect, the disclosure provides a method of treating disease, especially cancer, in a mammal, including a human, the method comprising administering to the mammal a therapeutically effective amount of polymorph form 1 of (7S,13R)-11-fluoro-7,13-dimethyl-6,7,13,14-tetrahydro-1,15-ethenopyrazolo[4,3-f][1,4,8,10]benzoxa-triazacyclotridecin-4(5H)-one, as described herein, or a pharmaceutical composition comprising polymorph form 1 of (7S,13R)-11-fluoro-7,13-dimethyl-6,7,13,14-tetrahydro-1,15-ethenopyrazolo[4,3-f][1,4,8,10]benzoxa-triazacyclotridecin-4(5H)-one, as described herein.

In one embodiment, the present disclosure provides a method of treating abnormal cell growth in a mammal, including a human, in need of such treatment comprising, administering to said mammal a therapeutically effective amount of the free base polymorph form 1 of Compound I. In another embodiment, the abnormal cell growth is mediated by at least one genetically altered tyrosine kinase.

In another embodiment, the abnormal cell growth is mediated by ALK, ROS1, TRK, JAK2, SRC, FAK or a combination thereof. In another embodiment, the abnormal cell growth is mediated by wild-type of mutant ALK. In another embodiment, the abnormal cell growth is mediated by wild-type of mutant ROS1. In another embodiment, the abnormal cell growth is mediated by wild-type of mutant TRK. In another embodiment, the abnormal cell growth is mediated by wild-type of mutant JAK2. In another embodiment, the abnormal cell growth is mediated by wild-type of mutant SRC. In another embodiment, the abnormal cell growth is mediated by wild-type of mutant FAK.

In another embodiment, the abnormal cell growth is cancer. In another embodiment, the cancer is selected from the group consisting of lung cancer, non-small cell lung cancer, small cell lung cancer, bone cancer, pancreatic cancer, skin cancer, cancer of the head or neck, hepatocellular carcinoma, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, gastric and esophagogastric cancers, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, such as anaplastic large cell lymphoma, cancer of the bladder, cancer of the kidney or ureter, renal cell carcinoma, carcinoma of the renal pelvis, neoplasms of the central nervous system (CNS), glioblastoma, primary CNS lymphoma, spinal axis tumors, brain stem glioma, pituitary adenoma, inflammatory myofibroblastic tumors, and combinations thereof.

In another aspect, the disclosure provides a compound of the formula II

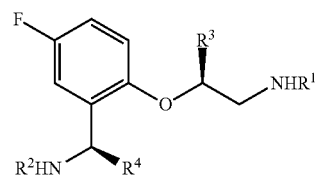

wherein $R^1$ and $R^2$ are each independently H or PG, and $R^3$ and $R^4$ are each independently $C_1$-$C_4$ alkyl.

In another aspect, the disclosure provides processes for preparing a compound of the formula B

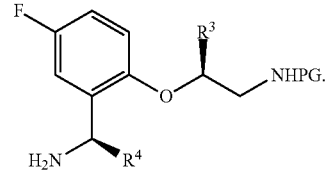

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A crystalline polymorph form of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one.

2. The crystalline polymorph form of clause 1, wherein the crystalline form is a polymorph form of the free base of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one.

3. The crystalline polymorph form of clause 1 or 2, wherein the crystalline polymorph form has a powder X-ray diffraction pattern comprising a peak at diffraction angle (2θ) of 27.4±0.1.

4. The crystalline polymorph form of any one of clauses 1 to 3, wherein the crystalline polymorph form has a powder X-ray diffraction pattern comprising peaks at diffraction angles (2θ) of 9.4±0.1 and 27.4±0.1.

5. The crystalline polymorph form of any one of clauses 1 to 4, wherein the crystalline polymorph form has a powder X-ray diffraction pattern comprising peaks at diffraction angles (2θ) of 9.4±0.1, 18.8±0.1, and 27.4±0.1.

6. The crystalline polymorph form of any one of clauses 1 to 5, wherein the crystalline polymorph form has a powder X-ray diffraction pattern comprising peaks at diffraction angles (2θ) of 9.4±0.1, 16.5±0.1, 18.8±0.1, and 27.4±0.1.

7. The crystalline polymorph form of any one of clauses 1 to 6, wherein the crystalline polymorph form has a powder X-ray diffraction pattern comprising peaks at diffraction angles (2θ) of 9.4±0.1, 16.5±0.1, 18.8±0.1, 22.8±0.1, and 27.4±0.1.

8. The crystalline polymorph form of any one of clauses 1 to 7, wherein the crystalline polymorph form has a powder X-ray diffraction pattern comprising peaks at diffraction angles (2θ) of 9.4±0.1, 16.1±0.1, 16.5±0.1, 18.8±0.1, 22.8±0.1, and 27.4±0.1.

9. The crystalline polymorph form of any one of clauses 1 to 8, wherein the crystalline polymorph form has a powder X-ray diffraction pattern comprising peaks at diffraction angles (2θ) of 9.4±0.1, 16.1±0.1, 16.5±0.1, 18.8±0.1, 21.2±0.1, 22.8±0.1, and 27.4±0.1.

10. A crystalline polymorph form of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one having a powder X-ray diffraction pattern substantially the same as shown in FIG. 1.

11. A pharmaceutical composition comprising the crystalline polymorph form of any one of the preceding claims.

12. A method of treating disease in a mammal, the method comprising administering to the mammal a therapeutically effective amount of the crystalline polymorph form of any one of clauses 1 to 10.

13. The method of clause 12, wherein the mammal is a human.

14. The method of clause 12 or 13, wherein the disease is selected from the group consisting of cancer, pain, neurological diseases, autoimmune diseases, and inflammation.

15. The method of any one of clauses 12 to 14, wherein the disease is cancer.

16. The method of clause 15, wherein the cancer is selected from the groups consisting of lung cancer, non-small cell lung cancer, small cell lung cancer, bone cancer, pancreatic cancer, skin cancer, cancer of the head or neck, hepatocellular carcinoma, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, gastric and esophago-gastric cancers, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, such as anaplastic large cell lymphoma, cancer of the bladder, cancer of the kidney or ureter, renal cell carcinoma, carcinoma of the renal pelvis, neoplasms of the central nervous system (CNS), glioblastoma, primary CNS lymphoma, spinal axis tumors, brain stem glioma, pituitary adenoma, inflammatory myofibroblastic tumors, and combinations thereof.

17. The method of clause 16, wherein the cancer is non-small cell lung cancer.

18. A compound of the formula II

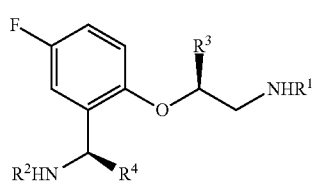

wherein $R^1$ and $R^2$ are each independently H or PG, and $R^3$ and $R^4$ are each independently a $C_1$-$C_4$ alkyl.

19. The compound of clause 18, wherein $R^1$ and $R^2$ are PG.

20. The compound of clause 18, wherein $R^2$ is H.

21. The compound of clause 18 or 19, wherein $R^1$ is H.

22. The compound of clause 18 or 20, wherein $R^1$ is PG.

23. The compound of clause 18 or 21, wherein $R^2$ is PG.

24. The compound of any one of clauses 18 to 23, wherein $R^3$ and $R^4$ are methyl.

25. The compound of any one of clauses 18 to 24, wherein PG is selected from the group consisting of FMOC, Boc, Cbz, Ac, trifluoroacetyl, phthalimide, Bn, trityl, benzylidene, and Ts.

26. The compound of any one of clauses 18 to 25, wherein PG is Boc.

27. A compound of the formula B-14

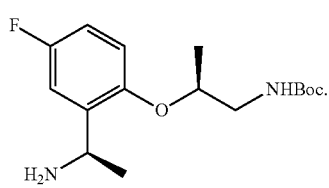

28. A process for preparing a compound of the formula I

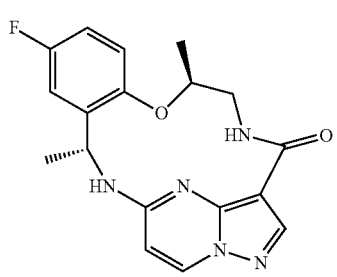

comprising
a. contacting a compound of the formula A

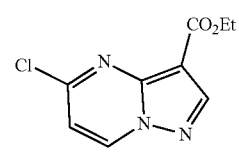

with a compound of the formula B-14

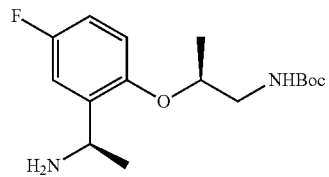

in the presence of a base to provide a compound of the formula C or

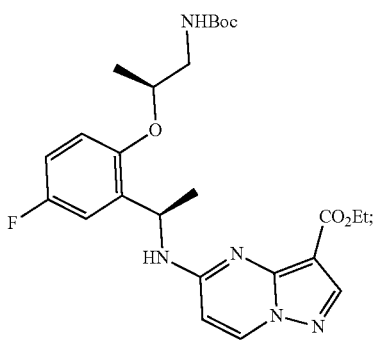

b. contacting a compound of the formula C with an inorganic base to provide a compound of the formula D

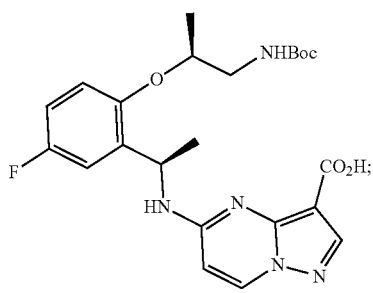

or c. contacting a compound of the formula D with an acid to provide a compound of the formula E

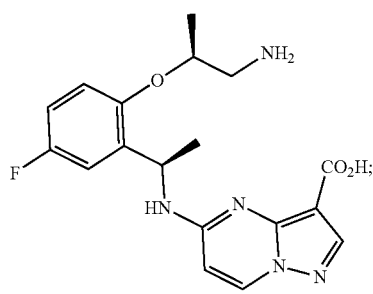

or d. contacting a compound of the formula E with a base in the presence of a phosphinate reagent to provide the compound of the formula I.

29. A process for preparing a compound of the formula B

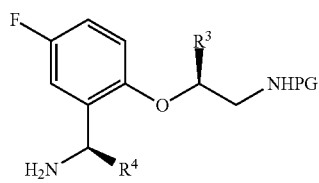

wherein

PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl;

comprising a. contacting a compound of the formula B-1

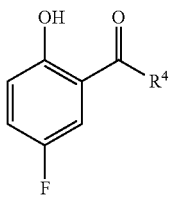

wherein $R^4$ is $C_1$-$C_4$ alkyl; with a compound of the formula B-2R

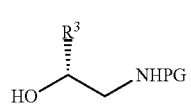

wherein $R^3$ is $C_1$-$C_4$ alkyl, and PG is selected from the group consisting of FMOC, Boc, Cbz, Ac, trifluoroacetyl, phthalimide, Bn, trityl, benzylidene, and Ts; in the presence of an azodicarboxylate reagent and a phosphine reagent to provide a compound of the formula B-3

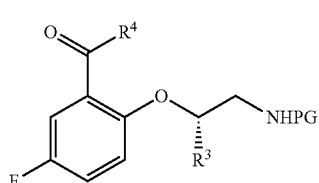

wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; or b. contacting a compound of the formula B-3

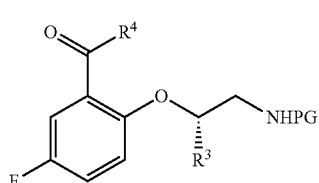

wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; with (R)-2-methyl-2-propanesulfinamide to provide a compound of the formula B-5

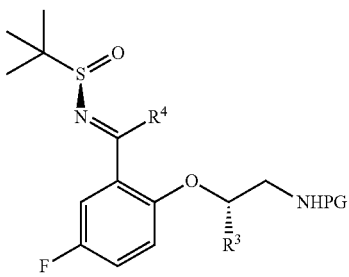

B-5 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; or c. contacting a compound of the formula B-5

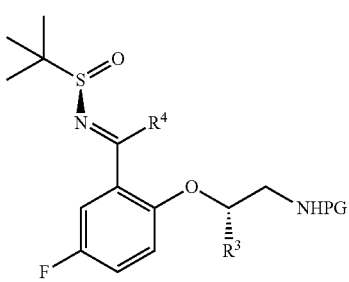

B-5 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; with a reducing agent to provide a compound of the formula B-6

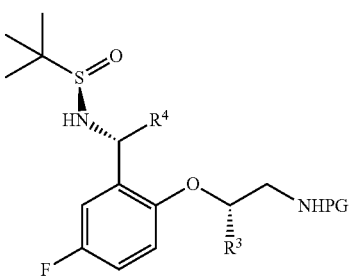

B-6 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; or d. contacting a compound of the formula B-6

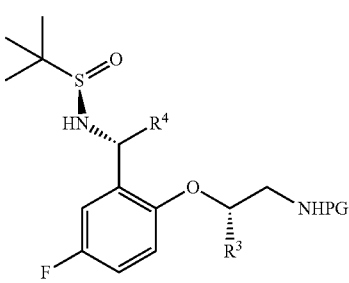

B-6 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; with an iodine reagent to provide a compound of the formula B.

30. A process for preparing a compound of the formula B

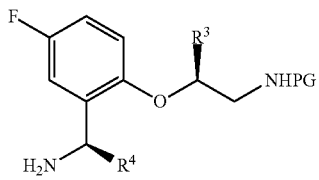

B wherein

PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl;

comprising a. reacting a compound of the formula B-7

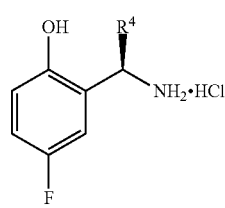

B-7 wherein $R^4$ is $C_1$-$C_4$ alkyl; under conditions suitable for preparing a compound of the formula B-8

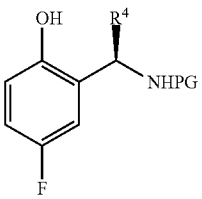

B-8 wherein $R^4$ is $C_1$-$C_4$ alkyl; and PG selected from the group consisting of FMOC, Boc, Cbz, Ac, trifluoroacetyl, phthalimide, Bn, trityl, benzylidene, and Ts; or b. contacting a compound of the formula B-8

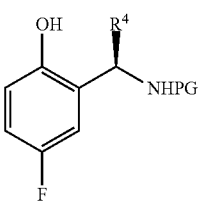

B-8 wherein $R^4$ is $C_1$-$C_4$ alkyl; and PG is selected from the group consisting of FMOC, Boc, Cbz, Ac, trifluoroacetyl, phthalimide, Bn, trityl, benzylidene, and Ts; with a compound of the formula B-2R with a compound of the formula B-2R

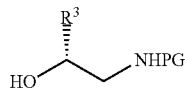
B-2R wherein R³ is C₁-C₄ alkyl, and PG is selected from the group consisting of FMOC, Boc, Cbz, Ac, trifluoroacetyl, phthalimide, Bn, trityl, benzylidene, and Ts; in the presence of an azodicarboxylate reagent and a phosphine reagent to provide a compound of the formula B-9

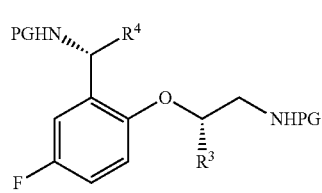
B-9 wherein each PG is independently selected from the group consisting of FMOC, Boc, Cbz, Ac, trifluoroacetyl, phthalimide, Bn, trityl, benzylidene, and Ts, provided that each PG is different; and R³ and R⁴ are each independently C₁-C₄ alkyl; or c. contacting a compound of the formula B-9

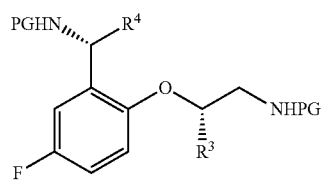
B-9 wherein each PG is independently selected from the group consisting of FMOC, Boc, Cbz, Ac, trifluoroacetyl, phthalimide, Bn, trityl, benzylidene, and Ts, provided that each PG is different; and R³ and R⁴ are each independently C₁-C₄ alkyl; with an inorganic base to provide a compound of the formula B.

31. A process for preparing a compound of the formula B

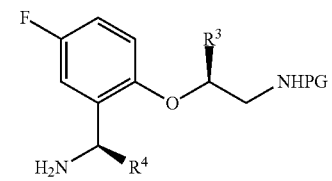
B wherein

PG is selected from the group consisting of FMOC, Boc, Cbz, Ac, trifluoroacetyl, phthalimide, Bn, trityl, benzylidene, and Ts; and R³ and R⁴ are each independently C₁-C₄ alkyl; comprising a. reacting a compound of the formula B-10

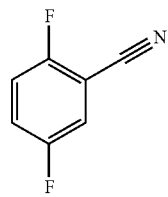
B-10 with a compound of the formula B-2S

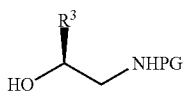
B-2S wherein R³ is C₁-C₄ alkyl, and PG is selected from the group consisting of FMOC, Boc, Cbz, Ac, trifluoroacetyl, phthalimide, Bn, trityl, benzylidene, and Ts; in the presence of a base to provide a compound of the formula B-11

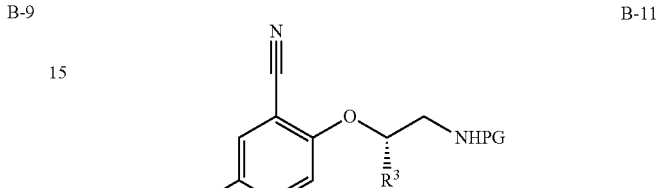
B-11 wherein R³ is C₁-C₄ alkyl, and PG is selected from the group consisting of FMOC, Boc, Cbz, Ac, trifluoroacetyl, phthalimide, Bn, trityl, benzylidene, and Ts; or b. contacting a compound of the formula B-11

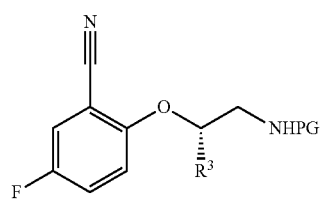
B-11 wherein R³ is C₁-C₄ alkyl, and PG is selected from the group consisting of FMOC, Boc, Cbz, Ac, trifluoroacetyl, phthalimide, Bn, trityl, benzylidene, and Ts; with a nucleophile to provide a compound of the formula B-12

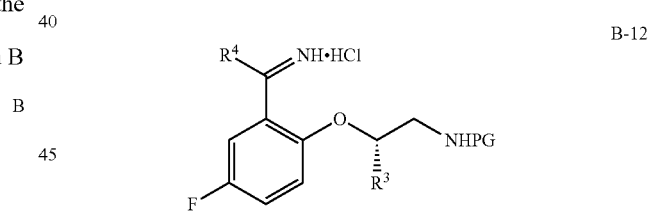
B-12 wherein R³ and R⁴ are each independently C₁-C₄ alkyl, and PG is selected from the group consisting of FMOC, Boc, Cbz, Ac, trifluoroacetyl, phthalimide, Bn, trityl, benzylidene, and Ts; or c. contacting a compound of the formula B-12

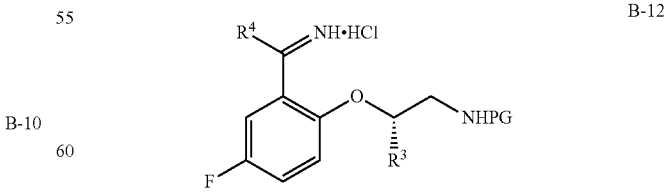
B-12 wherein R³ and R⁴ are each independently C₁-C₄ alkyl, and PG is selected from the group consisting of FMOC, Boc, Cbz, Ac, trifluoroacetyl, phthalimide, Bn, trityl, benzylidene, and Ts; with a reducing agent to provide a compound of the formula B.

30. A process for preparing a compound of the formula B

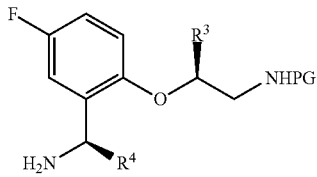

B wherein
PG is selected from the group consisting of FMOC, Boc, Cbz, Ac, trifluoroacetyl, phthalimide, Bn, trityl, benzylidene, and Ts; and
$R^3$ and $R^4$ are each independently $C_1$-$C_4$ alkyl;
comprising
a. reacting a compound of the formula B-12

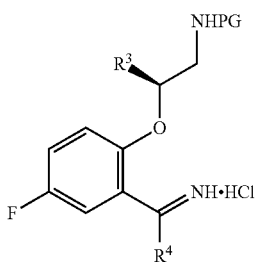

B-12 wherein PG is selected from the group consisting of FMOC, Boc, Cbz, Ac, trifluoroacetyl, phthalimide, Bn, trityl, benzylidene, and Ts; $R^3$ and $R^4$ are each independently $C_1$-$C_4$ alkyl; under conditions suitable for preparing a compound of the formula B-13

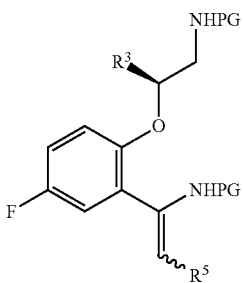

B-13 wherein each PG is independently selected from the group consisting of FMOC, Boc, Cbz, Ac, trifluoroacetyl, phthalimide, Bn, trityl, benzylidene, and Ts, provided that each PG is different; $R^3$ is $C_1$-$C_4$ alkyl; and $R^5$ is $C_1$-$C_3$ alkyl; or
b. contacting a compound of the formula B-13

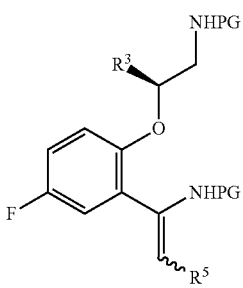

B-13 wherein each PG is independently selected from the group consisting of FMOC, Boc, Cbz, Ac, trifluoroacetyl, phthalimide, Bn, trityl, benzylidene, and Ts, provided that each PG is different; $R^3$ is $C_1$-$C_4$ alkyl; and $R^5$ is $C_1$-$C_3$ alkyl; with a reducing agent to provide a compound of the formula B-9

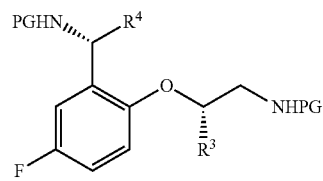

B-9 wherein each PG is independently selected from the group consisting of FMOC, Boc, Cbz, Ac, trifluoroacetyl, phthalimide, Bn, trityl, benzylidene, and Ts, provided that each PG is different; and $R^3$ and $R^4$ are each independently $C_1$-$C_4$ alkyl; or
c. contacting a compound of the formula B-9

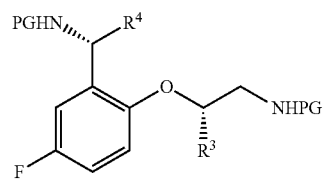

B-9 wherein each PG is independently selected from the group consisting of FMOC, Boc, Cbz, Ac, trifluoroacetyl, phthalimide, Bn, trityl, benzylidene, and Ts, provided that each PG is different; and $R^3$ and $R^4$ are each independently $C_1$-$C_4$ alkyl; with an inorganic base to provide a compound of the formula B.

Definitions

As used herein, the term "alkyl" includes a chain of carbon atoms, which is optionally branched and contains from 1 to 4 carbon atoms, and the like may be referred to as "lower alkyl." Illustrative alkyl groups include, but are not limited to, methyl, ethyl, n-propyl, isopropyl, n-butyl, isobutyl, sec-butyl, and tert-butyl.

As used herein, unless otherwise indicated, the term "abnormal cell growth" refers to cell growth that is independent of normal regulatory mechanisms (e.g., loss of contact inhibition).

As used herein, unless otherwise indicated, the term "treating" means reversing, alleviating, inhibiting the progress of (i.e. curative treatment), or preventing the disorder or condition to which such term applies, or one or more symptoms of such disorder or condition. The term "treatment", as used herein, unless otherwise indicated, refers to the act of treating as "treating" as defined immediately above. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

As used herein, the term "essentially the same" with reference to X-ray diffraction peak positions means that typical peak position and intensity variability are taken into account. For example, one skilled in the art will appreciate that the peak positions (2θ) will show some inter-apparatus variability, typically as much as 0.1°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

As used herein, the term "protecting group" or "PG" refers to any group as commonly known to one of ordinary skill in the art that can be introduced into a molecule by chemical modification of a functional group, such as an amine or hydroxyl, to obtain chemoselectivity in a subsequent chemical reaction. It will be appreciated that such protecting groups can be subsequently removed from the functional group at a later point in a synthesis to provide further opportunity for reaction at such functional groups or, in the case of a final product, to unmask such functional group. Protecting groups have been described in, for example, Wuts, P. G. M., Greene, T. W., Greene, T. W., & John Wiley & Sons. (2006). *Greene's protective groups in organic synthesis*. Hoboken, N.J.: Wiley-Interscience. One of skill in the art will readily appreciate the chemical process conditions under which such protecting groups can be installed on a functional group. Suitable amine protecting groups useful in connection with the present disclosure include, but are not limited to, 9-Fluorenylmethyl-carbonyl (FMOC), t-butylcarbonyl (Boc), benzyloxycarbonyl (Cbz), acetyl (Ac), trifluoroacetyl, phthalimide, benzyl (Bn), triphenylmethyl (trityl, Tr), benzylidene, and p-toluenesulfonyl (tosylamide, Ts).

DETAILED DESCRIPTION

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1:
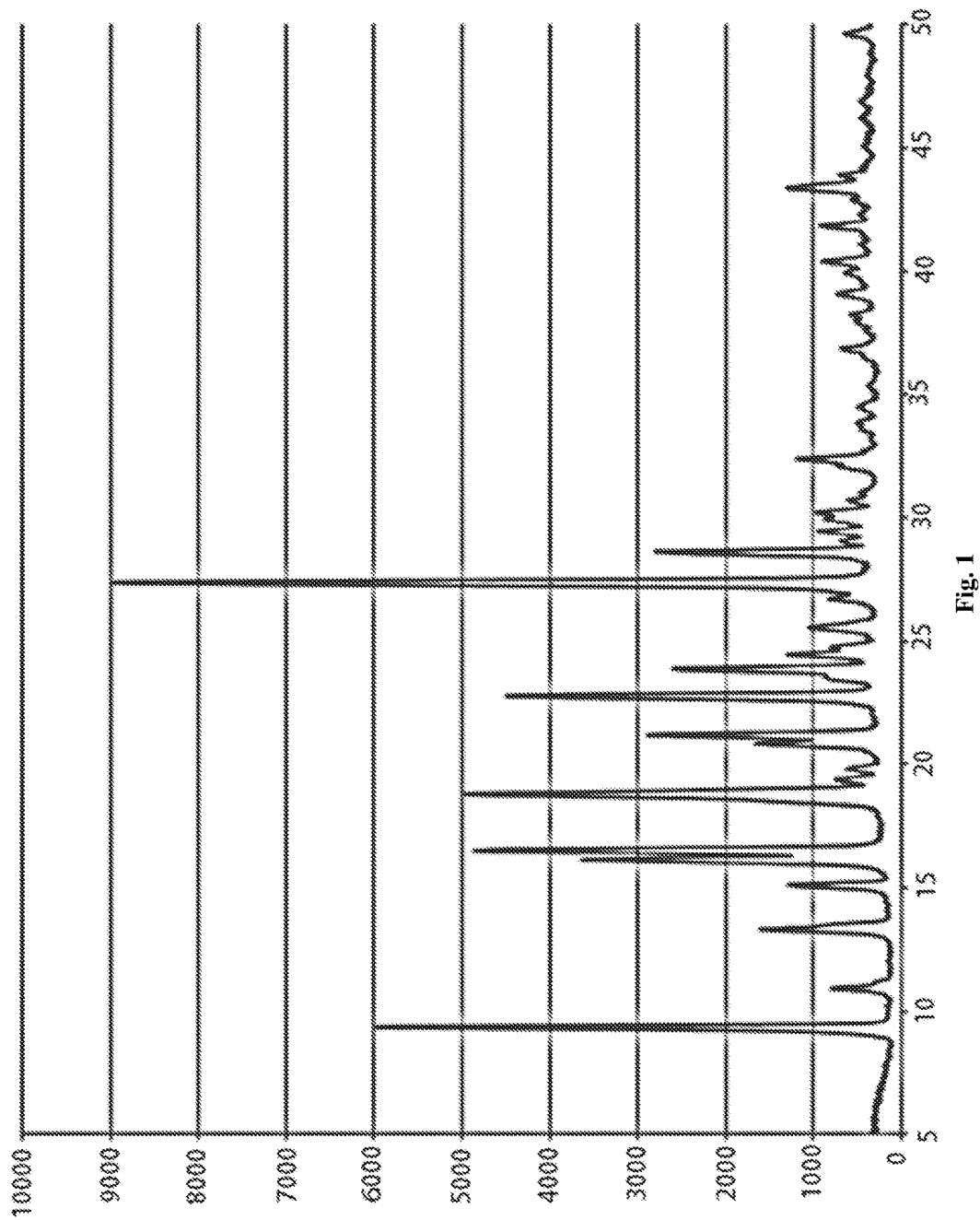
FIG. 1 shows a powder X-ray diffraction pattern of the crystalline form of free base (7S,13R)-11-fluoro-7,13-dimethyl-6,7,13,14-tetrahydro-1,15-ethenopyrazolo[4,3-f][1,4,8,10]benzoxa-triazacyclotridecin-4(5H)-one, polymorph form 1.

A unique physical form of the free base of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one has been prepared according to the methods described herein. The powder X-ray diffraction (PXRD) pattern of free base polymorph form 1 is shown in FIG. 1, with corresponding tabulated data shown in Table 1.

TABLE 1

| 2 θ | d-value | Peak Height | Peak intensity (%) |
|---|---|---|---|
| 9.4 | 0.94555 | 5982 | 50.7 |
| 10.9 | 0.80934 | 807 | 9.9 |
| 13.3 | 0.66425 | 1609 | 20.9 |
| 15.1 | 0.58566 | 1294 | 14.5 |
| 16.1 | 0.54960 | 3653 | 40.7 |
| 16.5 | 0.53704 | 4873 | 50.6 |
| 18.8 | 0.47191 | 4970 | 76.2 |
| 19.4 | 0.45746 | 761 | 9.7 |
| 19.8 | 0.44832 | 634 | 7.4 |
| 20.9 | 0.42579 | 1671 | 21.1 |
| 21.2 | 0.41905 | 2891 | 29.8 |
| 22.8 | 0.39036 | 4500 | 53.5 |
| 23.6 | 0.37762 | 875 | 9.4 |
| 23.9 | 0.37233 | 2600 | 32.5 |
| 24.5 | 0.36394 | 1307 | 15.5 |
| 24.8 | 0.35903 | 808 | 8.6 |
| 25.6 | 0.34853 | 1057 | 16.2 |
| 26.7 | 0.33392 | 842 | 10.6 |
| 27.4 | 0.32578 | 8974 | 100.0 |
| 28.6 | 0.31174 | 2804 | 35.2 |
| 29.1 | 0.30692 | 711 | 8.3 |
| 29.5 | 0.30325 | 961 | 11.4 |
| 29.9 | 0.29850 | 888 | 11.9 |
| 30.2 | 0.29561 | 976 | 11.2 |
| 30.7 | 0.29110 | 631 | 6.2 |
| 32.1 | 0.27908 | 708 | 4.5 |
| 32.4 | 0.27623 | 1200 | 17.2 |
| 33.9 | 0.26451 | 515 | 8.4 |
| 34.5 | 0.26005 | 512 | 8.0 |
| 36.9 | 0.24367 | 697 | 16.1 |
| 37.6 | 0.23930 | 438 | 3.7 |
| 38.0 | 0.23675 | 538 | 7.1 |
| 38.3 | 0.23521 | 598 | 5.9 |
| 39.1 | 0.23058 | 742 | 12.8 |
| 39.9 | 0.22592 | 658 | 15.7 |
| 40.4 | 0.22335 | 908 | 12.5 |
| 41.8 | 0.21589 | 941 | 12.0 |
| 42.9 | 0.21062 | 582 | 6.4 |
| 43.4 | 0.20849 | 1309 | 22.9 |
| 43.9 | 0.20615 | 720 | 6.8 |
| 49.6 | 0.18367 | 658 | 6.2 |

Figure 2:
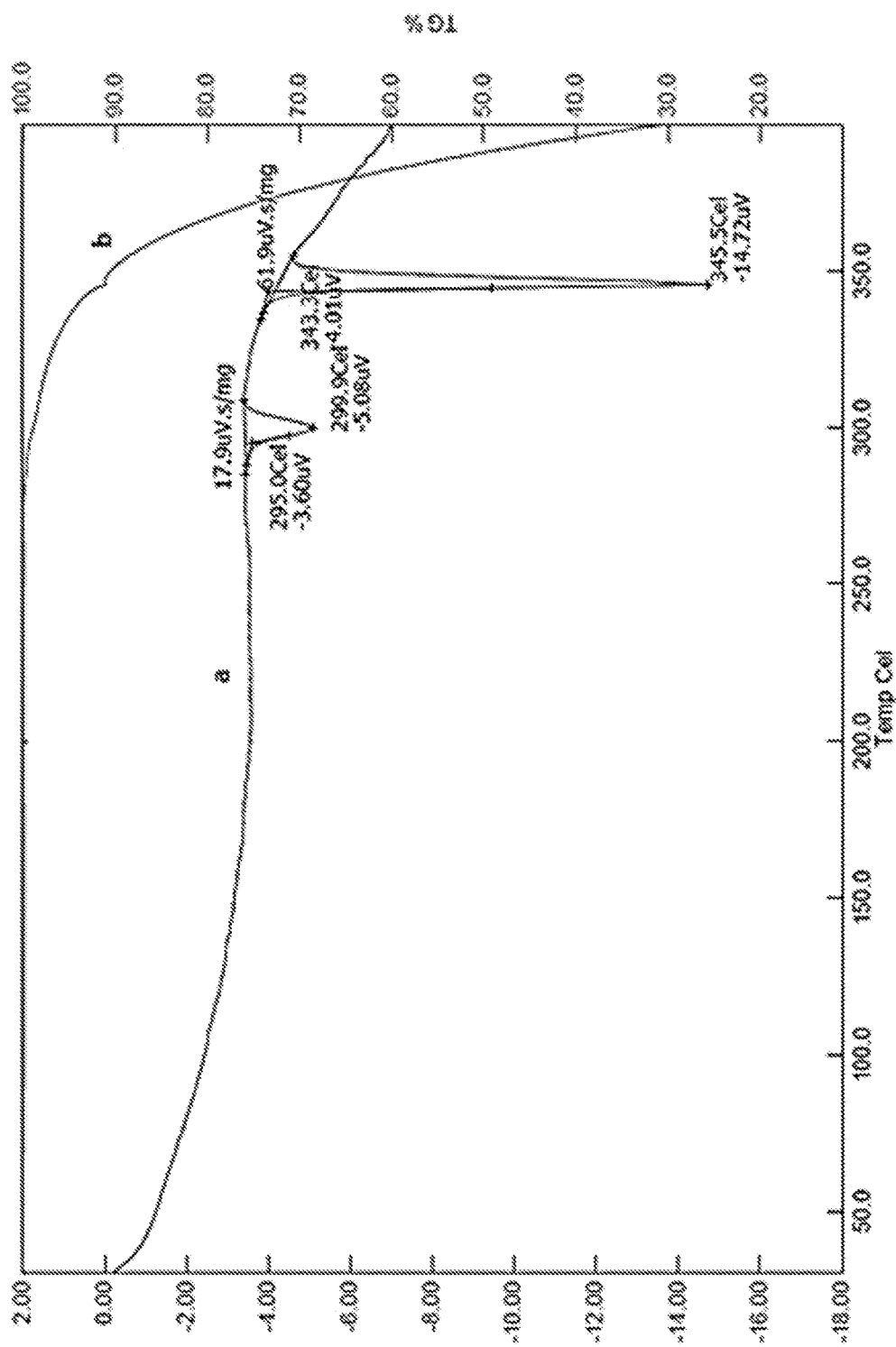
FIG. 2 shows a differential scanning calorimetery (DSC) thermogram of the crystalline form of free base (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, polymorph form 1. (a) TG curve; (b) TG % curve.

The DSC thermogram for crystalline polymorph form 1 is shown in FIG. 2.

In one aspect, the compounds and pharmaceutical compositions of the invention specifically target tyrosine receptor kinases, in particular ALK, ROS1, TRK, JAK2, SRC or FAK. Thus, these compounds and pharmaceutical compositions can be used to prevent, reverse, slow, or inhibit the activity of one or more of these kinases. In some embodiments, methods of treatment disease mediated by one or more receptor tyrosine kinase are described herein.

Exemplary diseases include cancer, pain, neurological diseases, autoimmune diseases, and inflammation.

In some embodiments, methods of treating cancer are described herein comprising administering a therapeutically effective amount of a crystalline polymorph form 1 of Compound I. Cancer includes but is not limited to lung cancer, such as non-small cell lung cancer, small cell lung cancer, and the like, bone cancer, pancreatic cancer, skin cancer, cancer of the head or neck, hepatocellular carcinoma, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, gastric and esophago-gastric cancers, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, such as anaplastic large cell lymphoma, cancer of the bladder, cancer of the kidney or ureter, renal cell carcinoma, carcinoma of the renal pelvis, neoplasms of the central nervous system (CNS), such as glioblastoma, primary CNS lymphoma, spinal axis tumors, brain stem glioma, and the like, pituitary adenoma, inflammatory myofibroblastic tumors, and combinations thereof. In other embodiments, methods are for treating lung cancer or non-small cell lung cancer.

In some embodiments, methods of treating or preventing pain are described herein comprising administering a therapeutically effective amount of a crystalline polymorph form 1 of Compound I. Pain includes, for example, pain from any source or etiology, including cancer pain, pain from chemotherapeutic treatment, nerve pain, pain from injury, or other sources.

In some embodiments, methods of treating autoimmune diseases are described herein comprising administering a therapeutically effective amount of a crystalline polymorph form 1 of Compound I. Autoimmune diseases include, for example, rheumatoid arthritis, Sjogren syndrome, Type I diabetes, and lupus. Exemplary neurological diseases include Alzheimer's Disease, Parkinson's Disease, Amyotrophic lateral sclerosis, and Huntington's disease.

In some embodiments, methods of treating inflammatory diseases of inflammation are described herein comprising administering a therapeutically effective amount of a crystalline polymorph form 1 of Compound I. Exemplary inflammatory diseases include atherosclerosis, allergy, and inflammation from infection or injury.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Pharmaceutical Compositions

The present disclosure also relates to pharmaceutical compositions comprising the free base polymorph form 1 of Compound I described herein. Pharmaceutical compositions of the present disclosure may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition may include conventional pharmaceutically-acceptable excipients. In addition, pharmaceutical compositions described herein may include other medicinal or pharmaceutical agents, carriers, adjuvants, etc.

A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. In some embodiments, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil.

Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

Drug Combinations

The inventive compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating the diseases and disorders described herein, including those active against another target associated with the disease. For example, compositions and formulations of the invention, as well as methods of treatment, can further comprise other drugs or pharmaceuticals, e.g., other active agents useful for treating or palliative for the target diseases or related symptoms or conditions. For cancer indications, additional such agents include, but are not limited to, kinase inhibitors, such as EGFR inhibitors (e.g., erlotinib, gefitinib), Raf inhibitors (e.g., vemurafenib), VEGFR inhibitors (e.g., sunitinib), ALK inhibitors (e.g., crizotinib) standard chemotherapy agents such as alkylating agents, antimetabolites, anti-tumor antibiotics, topoisomerase inhibitors, platinum drugs, mitotic inhibitors, antibodies, hormone therapies, or corticosteroids. For pain indications, suitable combination agents include anti-inflammatories such as NSAIDs. The pharmaceutical compositions of the invention may additional comprise one or more of such active agents, and methods of treatment may additionally comprise administering an effective amount of one or more of such active agents.

Synthesis Methods

In some embodiments, the disclosure provides a process for preparing a compound of the formula I

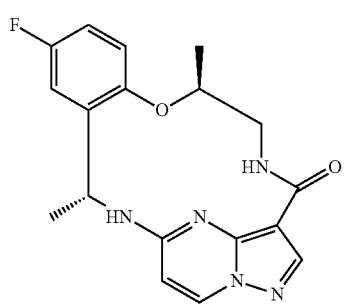

I comprising
(a) contacting a compound of the formula A

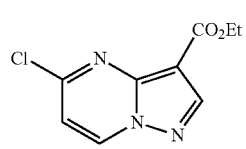

A with a compound of the formula B

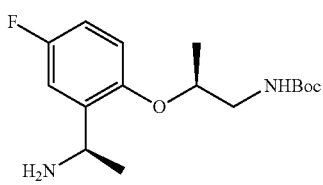

in the presence of a base to provide a compound of the formula C

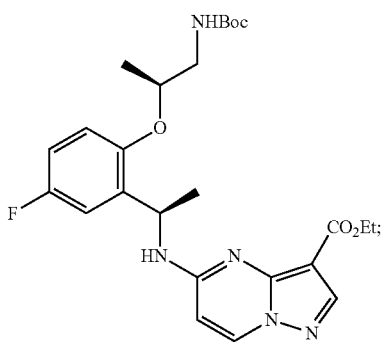

or (b) contacting a compound of the formula C with an inorganic base to provide a compound of the formula D

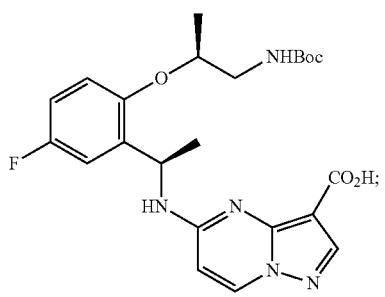

or (c) contacting a compound of the formula D with an acid to provide a compound of the formula E

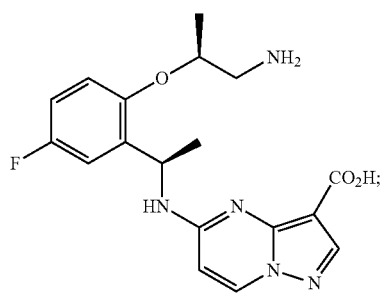

or (d) contacting a compound of the formula E with a base in the presence of a phosphinate reagent to provide the compound of the formula I.

It will be appreciated that the present disclosure provides processes for preparing a compound of the formula I described in the paragraphs above, comprising more than one of the step listed in the alternative. Accordingly, the present disclosure provides a process for preparing a compound of the formula I, comprising steps (a) and (b). Alternatively, the present disclosure provides a process for preparing a compound of the formula I, comprising steps (b) and (c). Alternatively, the present disclosure provides a process for preparing a compound of the formula I, comprising steps (c) and (d). Alternatively, the present disclosure provides a process for preparing a compound of the formula I, comprising steps (a), (b) and (c). Alternatively, the present disclosure provides a process for preparing a compound of the formula I, comprising steps (b), (c) and (d). Alternatively, the present disclosure provides a process for preparing a compound of the formula I, comprising steps (a), (b), (c) and (d).

In the first step (a), the base can be any organic base, such as an amine base. Suitable amine bases include, but are not limited to, DIEA, TEA, tributylamine, 2,6-lutidine, 2,2,6,6-tetramethylguanidine, and the like. In some embodiments, step (a) can be carried out in the presence of a polar protic solvent, such as an alcohol solvent. Suitable polar protic solvents include, but are not limited to, MeOH, EtOH, iPrOH, n-BuOH, sec-BuOH, and the like. In some embodiments, the polar protic solvent is n-BuOH. In some embodiments, step (a) can be carried out at a temperature of from about 50° C. to about 150° C. In some embodiments, the temperature is about 120° C.

In step (b), the inorganic base can be any inorganic base, such as a hydroxide base. Suitable hydroxide bases include, but are not limited to, sodium hydroxide, lithium hydroxide, and the like. In some embodiments, step (b) can be carried out in the presence of a polar protic solvent, a polar aprotic solvent or a mixture thereof. Suitable polar protic solvents include, but are not limited to, MeOH, EtOH, iPrOH, n-BuOH, sec-BuOH, $H_2O$, and the like. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, step (b) can be carried out in a mixture of solvents, such as THF/MeOH/$H_2O$. In some embodiments, step (b) can be carried out at a temperature of from about 30° C. to about 100° C. In some embodiments, the temperature is about 70° C.

In step (c), the acid can be a strong inorganic acid, such as HCl, such as 2M HCl. In some embodiments, the acid can be a solution of a strong acid in a polar aprotic solvent, such as $Et_2O$. For example, a suitable acid for use in step (c) can include 2M HCl in $Et_2O$. In some embodiments, step (c) can be carried out in the presence of a further polar aprotic solvent. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is DCM. In some embodiments, step (a) can be carried out at a temperature of from about 0° C. to about 50° C. In some embodiments, the temperature is about 25° C.

In the first step (d), the base can be any organic base, such as an amine base. Suitable amine bases include, but are not limited to, DIEA, TEA, tributylamine, 2,6-lutidine, 2,2,6,6-tetramethylguanidine, and the like. Suitable phosphinate reagents include those known to one of skill in the art that are useful in preparing an activated ester of a carboxylic acid, such as pentafluorophenyl diphenylphosphinate (FDPP). In some embodiments, step (d) can be carried out in the presence of a further polar aprotic solvent or a mixture of polar aprotic solvents. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is a mixture of DMF and DCM. In some embodiments, step (a) can be carried out at a temperature of from about −20° C. to about 50° C. In some embodiments, the temperature is about 0° C. to about 25° C.

In some embodiments, the disclosure provides a process (Method A) for preparing a compound of the formula B

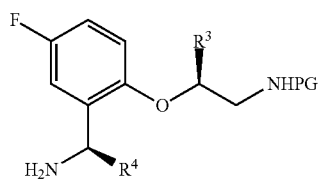

B wherein
PG is selected from the group consisting of FMOC, Boc, Cbz, Ac, trifluoroacetyl, phthalimide, Bn, trityl, benzylidene, and Ts; and
$R^3$ and $R^4$ are each independently $C_1$-$C_4$ alkyl;
comprising
(a) contacting a compound of the formula B-1

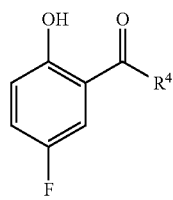

B-1 wherein $R^4$ is $C_1$-$C_4$ alkyl; with a compound of the formula B-2R

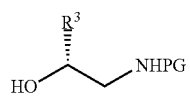

B-2R wherein $R^3$ is $C_1$-$C_4$ alkyl, and PG is selected from the group consisting of FMOC, Boc, Cbz, Ac, trifluoroacetyl, phthalimide, Bn, trityl, benzylidene, and Ts; in the presence of an azodicarboxylate reagent and a phosphine reagent to provide a compound of the formula B-3

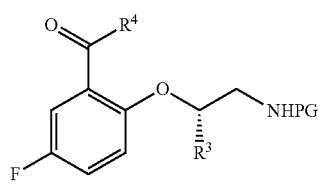

B-3 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; or (b) contacting a compound of the formula B-3

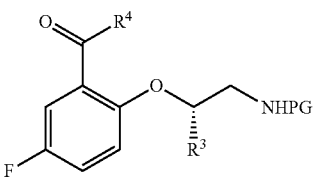

B-3 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; with (R)-2-methyl-2-propanesulfinamide to provide a compound of the formula B-5

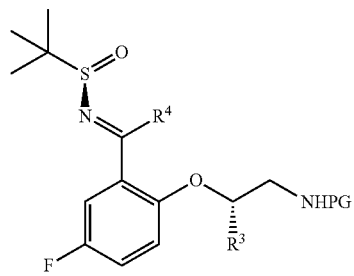

B-5 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; or (c) contacting a compound of the formula B-5

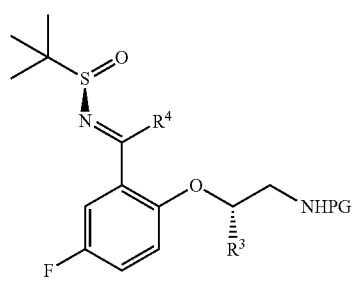

B-5 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; with a reducing agent to provide a compound of the formula B-6

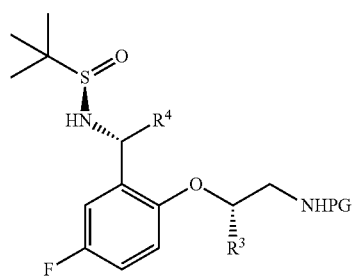

B-6 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; or (d) contacting a compound of the formula B-6

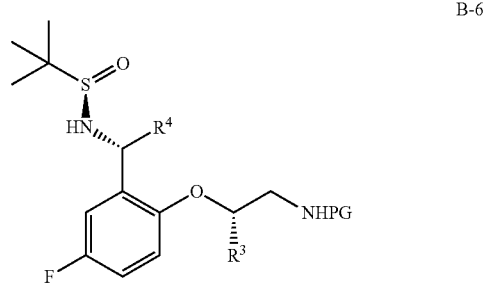

B-6 wherein PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl; with an iodine reagent to provide a compound of the formula B.

It will be appreciated that the present disclosure provides processes for preparing a compound of the formula B according to Method A as described in the paragraphs above, comprising more than one of the step listed in the alternative. Accordingly, the present disclosure provides a process for preparing a compound of the formula B, comprising steps (a) and (b). Alternatively, the present disclosure provides a process for preparing a compound of the formula B, comprising steps (b) and (c). Alternatively, the present disclosure provides a process for preparing a compound of the formula B, comprising steps (c) and (d). Alternatively, the present disclosure provides a process for preparing a compound of the formula B, comprising steps (a), (b) and (c). Alternatively, the present disclosure provides a process for preparing a compound of the formula B, comprising steps (b), (c) and (d). Alternatively, the present disclosure provides a process for preparing a compound of the formula B, comprising steps (a), (b), (c) and (d).

In step (a) of Method A, the azodicarboxylate reagent can be any such reagent known in the art. Suitable azodicarboxylate reagents include, but are not limited to, DEAD, diisopropyl azodicarboxylate (DIAD), di-(4-chlorobenzyl) azodicarboxylate (DCAD), and the like. In step (a) of Method A, the phosphine reagent can be any organophosphine reagent commonly known in the art, including, but not limited to triphenylphoshine, tributylphosphine, and the like. In some embodiments, step (a) of Method A can be carried out in the presence of a polar aprotic solvent. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is DCM. In some embodiments, step (a) of Method A can be carried out at a temperature of from about −20° C. to about 50° C. In some embodiments, the temperature is about 0° C. to about 25° C. In some embodiments, $R^3$ and $R^4$ are each methyl. In some embodiments, PG is Boc.

In some embodiments, a compound of the formula B-2 can be prepared by contacting (R)-1-aminopropan-2-ol with $(Boc)_2O$ in the presence of an amine base.

In some embodiments, step (b) of Method A can be carried out in the presence of a Lewis acid. In some embodiments, step (b) of Method A can be carried out in the presence of a water scavenger. In some embodiments, the Lewis acid and water scavenger can be the same reagent. In some embodiments, the Lewis acid and water scavenger can be different reagents. Suitable Lewis acids include, but are not limited to, copper (II) sulfate, magnesium sulfate, tetraethoxytitanium, tetraisopropxytitanium, and the like. Suitable water scavengers include, but are not limited to pyridinium p-toluenesulfonate, magnesium sulfate, sodium sulfate, tetraethoxytitanium, tetraisopropxytitanium, and the like. In some embodiments, the Lewis acid and water scavenger is tetraethoxytitanium. In some embodiments, step (b) of Method A can be carried out in the presence of a polar aprotic solvent. In some embodiments, step (b) of Method A can be carried out in the presence of a mixture of polar aprotic solvents. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is a mixture of THF and 2-methyl-THF. In some embodiments, step (b) of Method A can be carried out at a temperature of from about 0° C. to about 80° C. In some embodiments, the temperature is about 15° C. to about 65° C. In some embodiments, $R^3$ and $R^4$ are each methyl. In some embodiments, PG is Boc.

In step (c) of Method A, the reducing agent can be any element or compound commonly known in the art that loses (or "donates") an electron to another chemical species in a redox chemical reaction, including but not limited hydride reagents, elemental hydrogen, silane reagents, Hantzsch ester reagents, and the like. Suitable reducing agents include, but are not limited to, $NaBH_4$, $LiAlH_4$, and $H_2$. In some embodiments, the reducing agent in step (c) of Method A is $NaBH_4$. In some embodiments, step (c) of Method A can be carried out in the presence of a polar organic solvent. In some embodiments, step (c) of Method A can be carried out in the presence of a mixture of polar organic solvents. In some embodiments, the polar organic solvent or mixture of polar organic solvents can be polar aprotic or polar protic. Suitable polar aprotic solvents include, but are not limited to THF, 2-methyl-THF, $Et_2O$, DCM, EtOAc, DMF, $CH_3CN$, acetone, HMPT, DMSO, and the like. Suitable polar protic solvents include, but are not limited to, MeOH, EtOH, iPrOH, n-BuOH, sec-BuOH, $H_2O$, and the like. In some embodiments, the polar aprotic solvent is a mixture of THF and $H_2O$. In some embodiments, step (c) of Method A can be carried out at a temperature of from about −78° C. to about 30° C. In some embodiments, the temperature is about −50° C. to about 25° C. In some embodiments, $R^3$ and $R^4$ are each methyl. In some embodiments, PG is Boc.

In step (d) of Method A, the iodine reagent can be any iodine reagent known in the art useful for deprotection of a sulfinamide. In some embodiments, the iodine reagent is $I_2$. In some embodiments, step (d) of Method A can be carried out in the presence of a polar organic solvent. In some embodiments, step (d) of Method A can be carried out in the presence of a mixture of polar organic solvents. In some embodiments, the polar organic solvent or mixture of polar organic solvents can be polar aprotic or polar protic. Suitable polar aprotic solvents include, but are not limited to THF, 2-methyl-THF, $Et_2O$, DCM, EtOAc, DMF, $CH_3CN$, acetone, HMPT, DMSO, and the like. Suitable polar protic solvents include, but are not limited to, MeOH, EtOH, iPrOH, n-BuOH, sec-BuOH, $H_2O$, and the like. In some embodiments, the polar aprotic solvent is a mixture of THF and $H_2O$. In some embodiments, step (d) of Method A can be carried out at a temperature of from about 0° C. to about 80° C. In some embodiments, the temperature is about 25° C. to about 60° C. In some embodiments, the temperature is about 0° C. In some embodiments, $R^3$ and $R^4$ are each methyl. In some embodiments, PG is Boc.

Alternatively, in some embodiments, the disclosure provides a process (Method B) for preparing a compound of the formula B

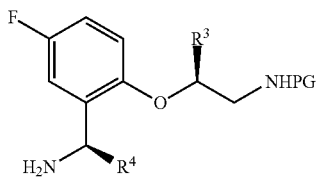

wherein
PG is selected from the group consisting of FMOC, Boc, Cbz, Ac, trifluoroacetyl, phthalimide, Bn, trityl, benzylidene, and Ts; and
$R^3$ and $R^4$ are each independently $C_1$-$C_4$ alkyl;
comprising
(a) reacting a compound of the formula B-7

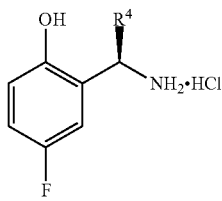

wherein $R^4$ is $C_1$-$C_4$ alkyl; under conditions suitable for preparing a compound of the formula B-8

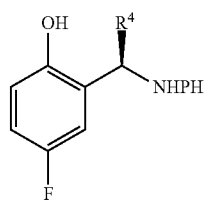

wherein $R^4$ is $C_1$-$C_4$ alkyl; and PG is selected from the group consisting of FMOC, Boc, Cbz, Ac, trifluoroacetyl, phthalimide, Bn, trityl, benzylidene, and Ts; or
(b) contacting a compound of the formula B-8

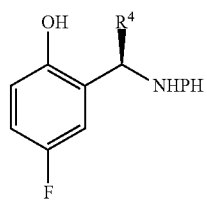

wherein $R^4$ is $C_1$-$C_4$ alkyl; and PG is selected from the group consisting of FMOC, Boc, Cbz, Ac, trifluoroacetyl, phthalimide, Bn, trityl, benzylidene, and Ts; with a compound of the formula B-2R

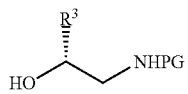

wherein $R^3$ is $C_1$-$C_4$ alkyl, and PG is selected from the group consisting of FMOC, Boc, Cbz, Ac, trifluoroacetyl, phthalimide, Bn, trityl, benzylidene, and Ts; in the presence of an azodicarboxylate reagent and a phosphine reagent to provide a compound of the formula B-9

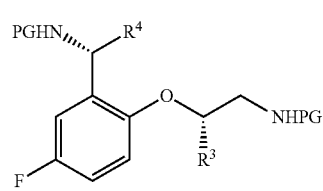

wherein each PG is independently selected from the group consisting of FMOC, Boc, Cbz, Ac, trifluoroacetyl, phthalimide, Bn, trityl, benzylidene, and Ts, provided that each PG is different; and $R^3$ and $R^4$ are each independently $C_1$-$C_4$ alkyl; or
(c) contacting a compound of the formula B-9

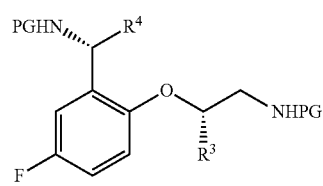

wherein each PG is independently selected from the group consisting of FMOC, Boc, Cbz, Ac, trifluoroacetyl, phthalimide, Bn, trityl, benzylidene, and Ts, provided that each PG is different; and $R^3$ and $R^4$ are each independently $C_1$-$C_4$ alkyl; with an inorganic base to provide a compound of the formula B.

It will be appreciated that the present disclosure provides processes for preparing a compound of the formula B according to Method B as described in the paragraphs above, comprising more than one of the step listed in the alternative. Accordingly, the present disclosure provides a process for preparing a compound of the formula B, comprising steps (a) and (b). Alternatively, the present disclosure provides a process for preparing a compound of the formula B, comprising steps (b) and (c). Alternatively, the present disclosure provides a process for preparing a compound of the formula B, comprising steps (a), (b) and (c).

In step (a) of Method B, a compound of the formula B-7 can be reacted under conditions suitable to introduce an amine protecting group (or PG). It will be appreciated that such conditions are commonly known to one of skill in the art, and any such conditions compatible with the functionality of a compound of the formula B-7 and the remainder of the process described in method B can be used. Suitable protecting groups (or PG) include, but are not limited to, FMOC, Boc, Cbz, Ac, trifluoroacetyl, phthalimide, Bn, trityl, benzylidene, and Ts. In some embodiments, PG is trifluoroacetyl. In some embodiments, a compound of the formula B-7 can be reacted under conditions suitable to introduce a trifluoroacetyl.

In some embodiments, step (a) of Method B involves contacting a compound of the formula B-7 with trifluoroacetic anhydride in the presence of an organic base, such as an amine base. Suitable amine bases include, but are not limited to, DIEA, TEA, tributylamine, 2,6-lutidine, 2,2,6,6-tetramethylguanidine, and the like. In some embodiments, step (a) of Method B can be carried out in a polar aprotic solvent. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is DCM. In some embodiments, step (a) of Method B can be carried out at a temperature of from about −20° C. to about 25° C. In some embodiments, the temperature is about 0° C. In some embodiments, $R^4$ is methyl. In some embodiments, PG is trifluoroacetyl.

In step (b), of Method B, the azodicarboxylate reagent can be any such reagent known in the art. Suitable azodicarboxylate reagents include, but are not limited to, DEAD, diisopropyl azodicarboxylate (DIAD), di-(4-chlorobenzyl) azodicarboxylate (DCAD), and the like. In step (b) of Method B, the phosphine reagent can be any organophosphine reagent commonly known in the art, including, but not limited to triphenylphoshine, tributylphosphine, and the like. In some embodiments, step (b) of Method B can be carried out in the presence of a polar aprotic solvent. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is DCM. In some embodiments, step (b) of Method B can be carried out at a temperature of from about −20° C. to about 50° C. In some embodiments, the temperature is about 0° C. to about 25° C. In some embodiments, $R^3$ and $R^4$ are each methyl. In some embodiments, one PG is Boc and one PG if trifluoroacetyl.

In some embodiments, step (c) of Method B can be carried out under conditions suitable to remove one of the PG groups in a compound of the formula B-9, while the other PG group remains intact. In step (c) of Method B, the inorganic base can be any inorganic base, such as a hydroxide base. Suitable hydroxide bases include, but are not limited to, sodium hydroxide, lithium hydroxide, and the like. In some embodiments, step (c) of Method B can be carried out in the presence of a polar protic solvent, a polar aprotic solvent, or a mixture thereof. Suitable polar protic solvents include, but are not limited to, MeOH, EtOH, iPrOH, n-BuOH, sec-BuOH, $H_2O$, and the like. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, step (c) of Method B can be carried out in a mixture of solvents, such as THF/MeOH. In some embodiments, step (c) of Method B can be carried out at a temperature of from about 30° C. to about 100° C. In some embodiments, the temperature is about 50° C. In some embodiments, $R^3$ and $R^4$ are each methyl. In some embodiments, one PG is Boc and one PG if trifluoroacetyl.

Alternatively, in some embodiments, the disclosure provides a process (Method C) for preparing a compound of the formula B

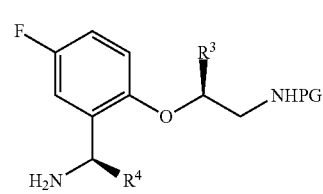

wherein
PG is selected from the group consisting of FMOC, Boc, Cbz, Ac, trifluoroacetyl, phthalimide, Bn, trityl, benzylidene, and Ts; and
$R^3$ and $R^4$ are each independently $C_1$-$C_4$ alkyl;
comprising
(a) reacting a compound of the formula B-10

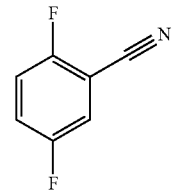

with a compound of the formula B-2S

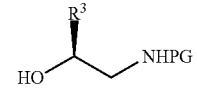

wherein $R^3$ is $C_1$-$C_4$ alkyl, and PG is selected from the group consisting of FMOC, Boc, Cbz, Ac, trifluoroacetyl, phthalimide, Bn, trityl, benzylidene, and Ts; in the presence of a base to provide a compound of the formula B-11

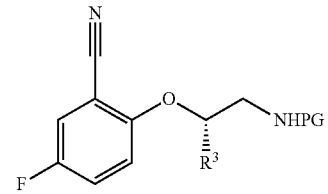

wherein $R^3$ is $C_1$-$C_4$ alkyl, and PG is selected from the group consisting of FMOC, Boc, Cbz, Ac, trifluoroacetyl, phthalimide, Bn, trityl, benzylidene, and Ts; or
(b) contacting a compound of the formula B-11

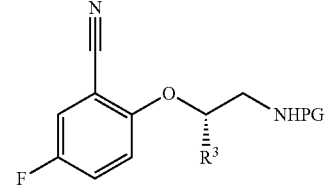

wherein $R^3$ is $C_1$-$C_4$ alkyl, and PG is selected from the group consisting of FMOC, Boc, Cbz, Ac, trifluoroacetyl, phthalimide, Bn, trityl, benzylidene, and Ts; with a nucleophile to provide a compound of the formula B-12

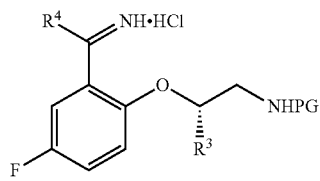

wherein $R^3$ and $R^4$ are each independently $C_1$-$C_4$ alkyl, and PG is selected from the group consisting of FMOC, Boc, Cbz, Ac, trifluoroacetyl, phthalimide, Bn, trityl, benzylidene, and Ts; or (c) contacting a compound of the formula B-12

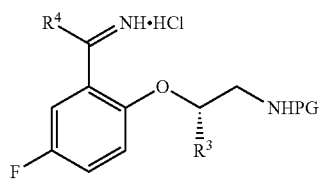

wherein $R^3$ and $R^4$ are each independently $C_1$-$C_4$ alkyl, and PG is selected from the group consisting of FMOC, Boc, Cbz, Ac, trifluoroacetyl, phthalimide, Bn, trityl, benzylidene, and Ts; with a reducing agent to provide a compound of the formula B.

It will be appreciated that the present disclosure provides processes for preparing a compound of the formula B according to Method C as described in the paragraphs above, comprising more than one of the step listed in the alternative. Accordingly, the present disclosure provides a process for preparing a compound of the formula B, comprising steps (a) and (b). Alternatively, the present disclosure provides a process for preparing a compound of the formula B, comprising steps (b) and (c). Alternatively, the present disclosure provides a process for preparing a compound of the formula B, comprising steps (a), (b) and (c).

In step (a) of Method C, the base can be any strong, non-nucleophilic base known to one of ordinary skill in the art. Suitable strong, non-nucleophilic bases include, but are not limited to, KHMDS, potassium tert-butoxide, lithium diisopropyl amide, 1,5,7-triazabicyclo(4.4.0)dec-5-ene (TBD), 7-methyl-1,5,7-triazabicyclo(4.4.0)dec-5-ene (MTBD), 1,8-diazabicyclo[5.4.0]-undec-7-ene (DBU), 1,5-diazabicyclo[4.3.0]non-5-ene (DBN), 1,1,3,3-tetramethylguanidine (TMG), and the like. In some embodiments, the strong, non-nucleophilic base is KHMDS. In some embodiments, step (a) of Method C can be carried out in the presence of a polar aprotic solvent. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is THF. In some embodiments, step (a) of Method C can be carried out at a temperature of from about $-20°$ C. to about $40°$ C. In some embodiments, the temperature is about $0°$ C. to about $25°$ C. In some embodiments, $R^3$ is methyl. In some embodiments, one PG is Boc.

In step (b) of Method C, the nucleophile can be any nucleophile capable of delivering a nucleophilic carbon atom to the nitrile functional group. Suitable nucleophiles include but are not limited to, alkyl metal halide reagents, such as Grignard reagents, and organolithium reagents. In some embodiments, the nucleophile in step (b) of method C is $C_1$-$C_4$ alkylMgBr. In some embodiments, the nucleophile in step (b) of method C is MeMgBr. In some embodiments, step (b) of Method C can be carried out in the presence of a polar aprotic solvent. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is THF. In some embodiments, step (b) of Method C further comprises the addition of an alcohol solvent, such as methanol or ethanol, to quench the reaction. In some embodiments, step (b) of Method C further comprises the addition a strong inorganic acid to form an imminium salt. In some embodiments, the strong acid is an HCl ether solution. In some embodiments, step (b) of Method C can be carried out at a temperature of from about $-80°$ C. to about $40°$ C. In some embodiments, the temperature is about $-78°$ C. to about $25°$ C. In some embodiments, $R^3$ and $R^4$ are methyl. In some embodiments, one PG is Boc.

In step (c) of Method C, the reducing agent can be any element or compound commonly known in the art that loses (or "donates") an electron to another chemical species in a redox chemical reaction, including but not limited hydride reagents, elemental hydrogen, silane reagents, Hantzsch ester reagents, and the like. Suitable reducing agents include, $H_2$ and Hantzsch ester. In some embodiments, it is convenient to contact the reducing agent in the presence of a catalyst, such as an iridium catalyst, a ruthenium catalyst, a rhodium catalyst, a palladium catalyst, and the like. It will be appreciated by one of skill in the art will that the catalyst can be any catalysts system known in the art that is capable of promoting the reduction of an imminium salt to an amine. In some embodiments, the catalyst is $[Ir(COD)Cl]_2$/(S, S)-f-binaphane. In some embodiments, the reducing agent in step (c) of Method C is $H_2$ in the presence of $[Ir(COD)Cl]_2$ and (S,S)-f-binaphane. In some embodiments, the $H_2$ is applied at from about 2 atmospheres of pressure to about 15 atmospheres of pressure. In some embodiments, the $H_2$ is applied at about 10 atmospheres of pressure.

In some embodiments, step (c) of Method C can be carried out in the presence of a polar protic solvent, such as an alcohol solvent. Suitable polar protic solvents include, but are not limited to, MeOH, EtOH, iPrOH, n-BuOH, sec-BuOH, and the like. In some embodiments, the polar protic solvent is MeOH. In some embodiments, step (c) of Method C can be carried out in the presence of a polar aprotic solvent. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is DCM. In some embodiments, step (c) of Method C can be carried out in a mixture of a polar protic solvent and a polar aprotic solvent. In some embodiments, step (c) of Method C can be carried out in a mixture of a DCM and MeOH.

Alternatively, in some embodiments, the disclosure provides a process (Method D) for preparing a compound of the formula B

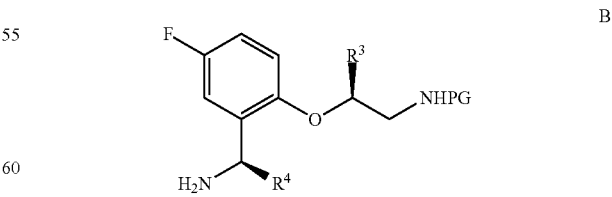

wherein

PG is selected from the group consisting of FMOC, Boc, Cbz, Ac, trifluoroacetyl, phthalimide, Bn, trityl, benzylidene, and Ts; and $R^3$ and $R^4$ are each independently $C_1$-$C_4$ alkyl;

comprising
(a) reacting a compound of the formula B-12

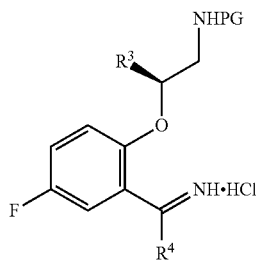

B-12 wherein PG is selected from the group consisting of FMOC, Boc, Cbz, Ac, trifluoroacetyl, phthalimide, Bn, trityl, benzylidene, and Ts; $R^3$ and $R^4$ are each independently $C_1$-$C_4$ alkyl; under conditions suitable for preparing a compound of the formula B-13

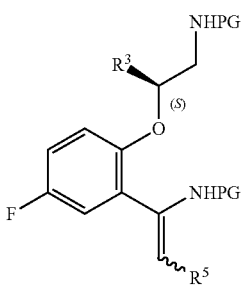

B-13 wherein each PG is independently selected from the group consisting of FMOC, Boc, Cbz, Ac, trifluoroacetyl, phthalimide, Bn, trityl, benzylidene, and Ts, provided that each PG is different; $R^3$ is $C_1$-$C_4$ alkyl; and $R^5$ is $C_1$-$C_3$ alkyl; or
(b) contacting a compound of the formula B-13

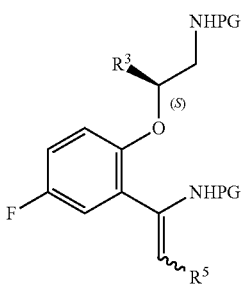

B-13 wherein each PG is independently selected from the group consisting of FMOC, Boc, Cbz, Ac, trifluoroacetyl, phthalimide, Bn, trityl, benzylidene, and Ts, provided that each PG is different; $R^3$ is $C_1$-$C_4$ alkyl; and $R^5$ is $C_1$-$C_3$ alkyl; with a reducing agent to provide a compound of the formula B-9

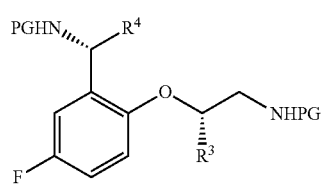

B-9 wherein each PG is independently selected from the group consisting of FMOC, Boc, Cbz, Ac, trifluoroacetyl, phthalimide, Bn, trityl, benzylidene, and Ts, provided that each PG is different; and $R^3$ and $R^4$ are each independently $C_1$-$C_4$ alkyl; or
(c) contacting a compound of the formula B-9

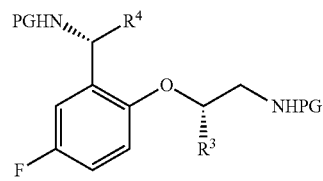

B-9 wherein each PG is independently selected from the group consisting of FMOC, Boc, Cbz, Ac, trifluoroacetyl, phthalimide, Bn, trityl, benzylidene, and Ts, provided that each PG is different; and $R^3$ and $R^4$ are each independently $C_1$-$C_4$ alkyl; with an inorganic base to provide a compound of the formula B.

It will be appreciated that the present disclosure provides processes for preparing a compound of the formula B according to Method D as described in the paragraphs above, comprising more than one of the step listed in the alternative. Accordingly, the present disclosure provides a process for preparing a compound of the formula B, comprising steps (a) and (b). Alternatively, the present disclosure provides a process for preparing a compound of the formula B, comprising steps (b) and (c). Alternatively, the present disclosure provides a process for preparing a compound of the formula B, comprising steps (a), (b) and (c).

In some embodiments, step (a) of Method D involves contacting a compound of the formula B-12 with trifluoroacetic anhydride in the presence of an organic base, such as an amine base. Suitable amine bases include, but are not limited to, DIEA, TEA, tributylamine, 2,6-lutidine, 2,2,6,6-tetramethylguanidine, and the like. In some embodiments, step (a) of Method D can be carried out in a polar aprotic solvent. Suitable polar aprotic solvents include, but are not limited to THF, 2-methyl-THF, $Et_2O$, DCM, EtOAc, DMF, $CH_3CN$, acetone, HMPT, DMSO, and the like. In some embodiments, the polar aprotic solvent is DCM. In some embodiments, step (a) of Method D can be carried out at a temperature of from about −20° C. to about 25° C. In some embodiments, the temperature is about 0° C. In some embodiments, $R^4$ is methyl. In some embodiments, PG is trifluoroacetyl.

In step (b) of Method D, the reducing agent can be any element or compound commonly known in the art that loses (or "donates") an electron to another chemical species in a redox chemical reaction, including but not limited hydride reagents, elemental hydrogen, silane reagents, Hantzsch ester reagents, and the like. Suitable reducing agents include, $H_2$ and Hantzsch ester. In some embodiments, it is convenient to contact the reducing agent in the presence of a catalyst, such as an iridium catalyst, a ruthenium catalyst, a rhodium catalyst, a palladium catalyst, and the like. It will be appreciated by one of skill in the art will that the catalyst can be any catalysts system known in the art that is capable of promoting the reduction of an imminium salt to an amine. In some embodiments, the catalyst is and [((R,R)-Me-DuPHOS)—Rh—(COD)]$BF_4$. In some embodiments, the reducing agent in step (b) of Method D is $H_2$ in the presence of and [((R,R)-Me-DuPHOS)—Rh—(COD)]$BF_4$. In some embodiments, the H$_2$ is applied at from about 2 psi to about 100 psi. In some embodiments, the H$_2$ is applied at about 90 psi.

In some embodiments, step (b) of Method D can be carried out in the presence of a polar protic solvent, such as an alcohol solvent. Suitable polar protic solvents include, but are not limited to, MeOH, EtOH, iPrOH, n-BuOH, sec-BuOH, and the like. In some embodiments, the polar protic solvent is MeOH. In some embodiments, step (b) of Method D can be carried out in the presence of a polar aprotic solvent. Suitable polar aprotic solvents include, but are not limited to THF, 2-methyl-THF, Et$_2$O, DCM, EtOAc, DMF, CH$_3$CN, acetone, HMPT, DMSO, and the like. In some embodiments, the polar aprotic solvent is DCM. In some embodiments, step (b) of Method D can be carried out in a mixture of a polar protic solvent and a polar aprotic solvent. In some embodiments, step (b) of Method D can be carried out in a mixture of a DCM and MeOH.

In some embodiments, step (c) of Method D can be carried out under conditions suitable to remove one of the PG groups in a compound of the formula B-9, while the other PG group remains intact. In step (c) of Method D, the inorganic base can be any inorganic base, such as a a carbonate base or a hydroxide. Suitable hydroxide bases include, but are not limited to, sodium hydroxide, lithium hydroxide, and the like. Suitable carbonate bases include, but are not limited to, potassium carbonate, sodium bicarbonate, sodium carbonate, and the like. In some embodiments, the inorganic base is potassium carbonate. In some embodiments, step (c) of Method D can be carried out in the presence of a polar protic solvent, a polar aprotic solvent, or a mixture thereof. Suitable polar protic solvents include, but are not limited to, MeOH, EtOH, iPrOH, n-BuOH, sec-BuOH, H$_2$O, and the like. Suitable polar aprotic solvents include, but are not limited to THF, 2-methyl-THF, Et$_2$O, DCM, EtOAc, DMF, CH$_3$CN, acetone, HMPT, DMSO, and the like. In some embodiments, step (c) of Method D can be carried out in MeOH. In some embodiments, step (c) of Method D can be carried out at a temperature of from about 30° C. to about 100° C. In some embodiments, the temperature is about 50° C. In some embodiments, R$^3$ and R$^4$ are each methyl. In some embodiments, one PG is Boc and one PG if trifluoroacetyl.

EXAMPLES

The examples and preparations provided below further illustrate and exemplify particular aspects of embodiments of the disclosure. It is to be understood that the scope of the present disclosure is not limited in any way by the scope of the following examples.

Abbreviations

The examples described herein use materials, including but not limited to, those described by the following abbreviations known to those skilled in the art:

| | |
|---|---|
| g | grams |
| eq | equivalents |
| mmol | millimoles |
| mol | moles |
| mL | milliliters |
| L | liters |
| psi | pounds per square inch |
| EtOAc or EA | ethyl acetate |
| MeCN | acetonitrile |
| DCM | dichloromethane |
| MTBE | methyl tert-butyl ether |
| DEAD | diethyl azodicarboxylate |
| DIAD | diisopropyl azodicarboxylate |
| [Ir(COD)Cl]$_2$ | bis(1,5-cyclooctadiene)di-μ-chlorodiiridium(I) |
| [((R,R)-Me-DuPHOS)-Rh-(COD)]BF$_4$ | 1,2-Bis((2R,5R)-2,5-dimethylphospholano)-benzene(cyclooctadiene)rhodium(I) tetrafluoroborate |
| MHz | megahertz |
| δ | chemical shift |
| THF | tetrahydrofuran |
| PE | petroleum ether |
| R$_f$ | retardation factor |
| DMSO-d$_6$ | deuterated dimethyl sulfoxide |
| CDCl$_3$ | deuterated chloroform |
| n-BuOH | n-butanol |
| DIEA or DIPEA or Hunig's Base | n,n-diisopropylethylamine |
| TEA | triethylamine |
| KHMDS | potassium bis(trimethylsilyl)amide |
| TMSCl | trimethylsilyl chloride |
| min or mins | minute or minutes |
| hrs, hr or h | hour or hours |
| TLC | thin layer chromatography |
| M | molar |
| MS | mass spectrum |
| m/z | mass-to-charge ratio |
| FDPP | pentafluorophenyl diphenylphosphinate |
| DMAP | 4-(dimethylamino)pyridine |
| DMF | N,N-dimethylformamide |
| IPC | ion-pair chromatography |
| LCMS | liquid chromatography mass spectrometry |

Synthesis of Crystalline Polymorph Form 1 of Compound I

Compound I was prepared according to the following synthetic scheme:

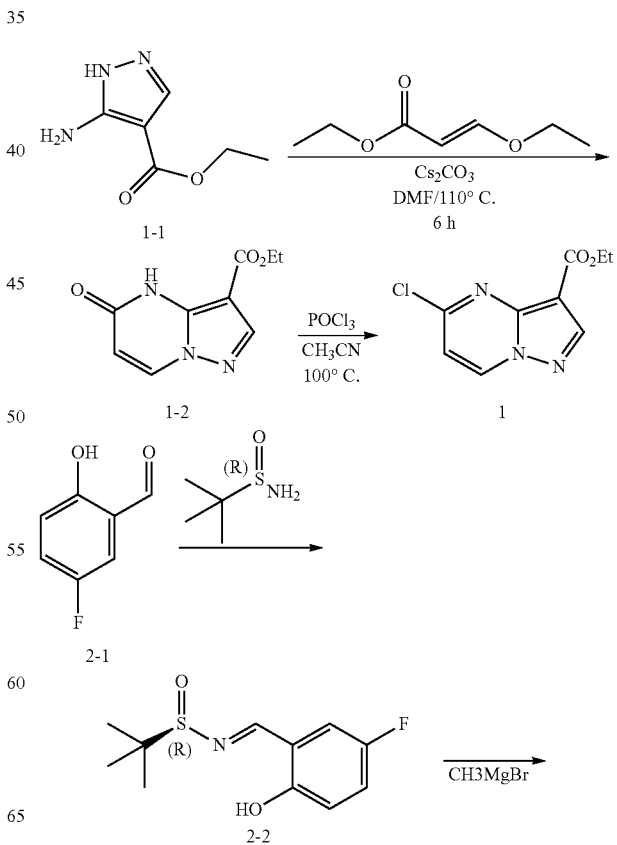

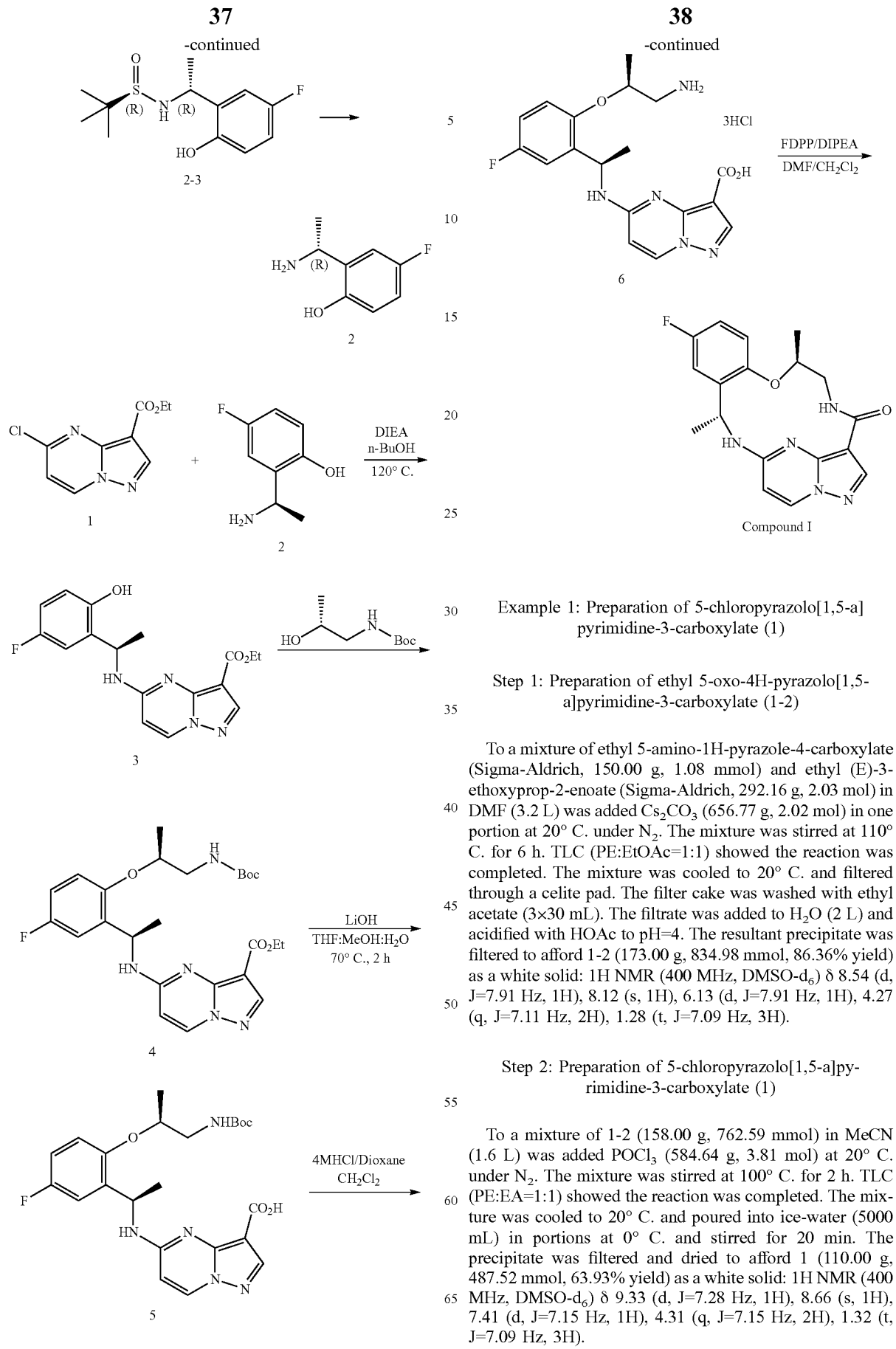

Example 1: Preparation of 5-chloropyrazolo[1,5-a]pyrimidine-3-carboxylate (1)

Step 1: Preparation of ethyl 5-oxo-4H-pyrazolo[1,5-a]pyrimidine-3-carboxylate (1-2)

To a mixture of ethyl 5-amino-1H-pyrazole-4-carboxylate (Sigma-Aldrich, 150.00 g, 1.08 mmol) and ethyl (E)-3-ethoxyprop-2-enoate (Sigma-Aldrich, 292.16 g, 2.03 mol) in DMF (3.2 L) was added $Cs_2CO_3$ (656.77 g, 2.02 mol) in one portion at 20° C. under $N_2$. The mixture was stirred at 110° C. for 6 h. TLC (PE:EtOAc=1:1) showed the reaction was completed. The mixture was cooled to 20° C. and filtered through a celite pad. The filter cake was washed with ethyl acetate (3×30 mL). The filtrate was added to $H_2O$ (2 L) and acidified with HOAc to pH=4. The resultant precipitate was filtered to afford 1-2 (173.00 g, 834.98 mmol, 86.36% yield) as a white solid: 1H NMR (400 MHz, DMSO-$d_6$) δ 8.54 (d, J=7.91 Hz, 1H), 8.12 (s, 1H), 6.13 (d, J=7.91 Hz, 1H), 4.27 (q, J=7.11 Hz, 2H), 1.28 (t, J=7.09 Hz, 3H).

Step 2: Preparation of 5-chloropyrazolo[1,5-a]pyrimidine-3-carboxylate (1)

To a mixture of 1-2 (158.00 g, 762.59 mmol) in MeCN (1.6 L) was added $POCl_3$ (584.64 g, 3.81 mol) at 20° C. under $N_2$. The mixture was stirred at 100° C. for 2 h. TLC (PE:EA=1:1) showed the reaction was completed. The mixture was cooled to 20° C. and poured into ice-water (5000 mL) in portions at 0° C. and stirred for 20 min. The precipitate was filtered and dried to afford 1 (110.00 g, 487.52 mmol, 63.93% yield) as a white solid: 1H NMR (400 MHz, DMSO-$d_6$) δ 9.33 (d, J=7.28 Hz, 1H), 8.66 (s, 1H), 7.41 (d, J=7.15 Hz, 1H), 4.31 (q, J=7.15 Hz, 2H), 1.32 (t, J=7.09 Hz, 3H).

Example 2: Preparation of (R)-2-(1-aminoethyl)-4-fluorophenol (2)

Step 1: Preparation of (R)—N-(5-fluoro-2-hydroxybenzylidene)-2-methylpropane-2-sulfinamide (2-2)

To a solution of (R)-2-methylpropane-2-sulfinamide (Sigma-Aldrich, 150.00 g, 1.24 mol, 1.00 eq.) and 5-fluoro-2-hydroxybenzaldehyde (2-1) (Sigma-Aldrich, 173.74 g, 1.24 mol, 1.00 eq.) in DCM (2.00 L) was added $Cs_2CO_3$ (646.43 g, 1.98 mol, 1.60 eq.). The mixture was stirred at 16° C. for 16 hours. TLC (PE:EtOAc=5:1) showed the reaction was completed. The reaction mixture was quenched by addition of $H_2O$ (1000 mL) at 0° C. and then extracted with EtOAc (500 mL×4). The combined organic layers were washed with brine (1000 mL) and dried over $Na_2SO_4$, filtered and concentrated under reduced pressure to give 2-2 (230.00 g, 945.33 mmol, 76.24% yield). $^1$HNMR (CDCl$_3$, 400 MHz) δ 8.64 (s, 1H), 7.22-7.11 (m, 2H), 7.03-6.95 (m, 1H), 1.28 (s, 9H).

Step 2: Preparation of (R)—N—((R)-1-(5-fluoro-2-hydroxyphenyl)ethyl)-2-methylpropane-2-sulfinamide (2-3R)

To a solution of (R)—N-(5-fluoro-2-hydroxybenzylidene)-2-methylpropane-2-sulfinamide (2-2) (200.00 g, 822.03 mmol, 1.00 eq.) in THF (2.5 L) was added MeMgBr (490.09 g, 4.11 mol, 5.00 eq.) drop-wise at −65° C. under $N_2$ over a period of 30 min. The mixture was then warmed to ambient temperature and stirred for 18 hours. TLC (PE:EtOAc=1:1) showed the reaction was complete with the production of two diastereomers. The reaction mixture was quenched by addition of $H_2O$ (2 L) at 0° C., the mixture was extracted with EtOAc (500 mL×3). The combined organic layers were washed with brine (500 mL), dried over $Na_2SO_4$, filtered and concentrated under reduced pressure to give a residue. The residue was purified by column chromatography (SiO$_2$, Petroleum ether/Ethyl acetate=50/1 to 1:1) to give (R)—N—((R)-1-(5-fluoro-2-hydroxyphenyl)ethyl)-2-methylpropane-2-sulfinamide (2-3R) (125 g, the top, less polar spot with Rf: 0.5, PE:EA=1:1). $^1$HNMR (CDCl$_3$, 400 MHz) δ: 9.17 (s, 1H), 6.68 (dd, J=3.0, 8.8 Hz, 1H), 6.47 (dt, J=3.0, 8.4 Hz, 1H), 6.31 (dd, J=4.8, 8.8 Hz, 1H), 5.11 (d, J=8.0 Hz, 1H), 4.28 (quin, J=7.2 Hz, 1H), 1.43 (d, J=6.8 Hz, 3H), 1.20 (s, 9H).

Step 3: Preparation of (R)-2-(1-aminoethyl)-4-fluorophenol (2)

A solution of (R)—N—((R)-1-(5-fluoro-2-hydroxyphenyl)ethyl)-2-methylpropane-2-sulfinamide (2-3R) (125 g, 481.99 mmol, 1.00 eq.) in HCl/dioxane (1.5 L, 4N) was stirred at ambient temperature for 2 hours. TLC (PE:EtOAc=2:1) showed the reaction was complete. The mixture was filtered to give (R)-2-(1-aminoethyl)-4-fluorophenol (2) HCl salt (85 g, 443.56 mmol, 90.03% yield) as a white solid. $^1$HNMR (d-DMSO, 400 MHz) δ 10.24 (s, 1H), 8.48 (br. s., 3H), 7.31 (dd, J=2.9, 9.7 Hz, 1H), 7.05-6.99 (m, 1H), 6.98-6.93 (m, 1H), 4.59-4.45 (m, 1H), 1.46 (d, J=6.8 Hz, 3H).

Example 3: Preparation of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (Compound I)

Step 1: Preparation of ethyl (R)-5-((1-(5-fluoro-2-hydroxyphenyl)ethyl)amino)pyrazolo[1,5-a]pyrimidine-3-carboxylate (3)

To a solution of (R)-2-(1-aminoethyl)-4-fluorophenol (2) (85 g, 443.56 mmol, 1.00 eq.) and ethyl 5-chloropyrazolo[1,5-a]pyrimidine-3-carboxylate (1) (100.08 g, 443.56 mmol, 1.00 eq.) in n-BuOH (2 L) was added DIEA (343.96 g, 2.66 mol, 6.00 eq.). The mixture was stirred at 120° C. for 2 hrs. TLC (PE:EtOAc=1:1) showed the reaction was completed. The reaction mixture was diluted with $H_2O$ (500 mL) at 16° C., and extracted with EtOAc (500 mL×3). The combined organic layers were washed with brine (500 mL), dried over $Na_2SO_4$, filtered and concentrated under reduced pressure to give a residue. The residue was purified by column chromatography (SiO$_2$, Petroleum ether/Ethyl acetate=10/1 to 1:3) to give ethyl (R)-5-((1-(5-fluoro-2-hydroxyphenyl)ethyl)amino)pyrazolo[1,5-a]pyrimidine-3-carboxylate (3) (122 g, 349.34 mmol, 78.76% yield, ee>99% purity) as a white solid. $^1$HNMR (CDCl$_3$, 400 MHz) δ 9.28 (br. s., 1H), 8.26 (s, 1H), 8.14 (d, J=7.5 Hz, 1H), 6.95-6.89 (m, 2H), 6.87-6.80 (m, 1H), 6.18 (d, J=7.5 Hz, 1H), 5.98 (d, J=8.3 Hz, 1H), 5.71-5.54 (m, 1H), 4.50-4.35 (m, 2H), 1.60 (d, J=6.8 Hz, 3H), 1.42 (t, J=7.2 Hz, 3H).

Step 2: Preparation of ethyl 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylate (4)

A mixture of ethyl (R)-5-((1-(5-fluoro-2-hydroxyphenyl)ethyl)amino)pyrazolo[1,5-a]pyrimidine-3-carboxylate (3) (10.00 g, 29.04 mmol) and tert-butyl (R)-(2-hydroxypropyl)carbamate (Combi-Blocks, 7.63 g, 43.56 mmol) was azetrope dried from DCM/toluene, and then re-dissolved in DCM (11.62 mL). To the solution was added $PPh_3$ (11.43 g, 43.56 mmol), and the mixture was stirred until the starting materials were completely dissolved. To the solution was added DEAD (8.81 g, 43.56 mmol) over 5 min with mixing. The reaction was stirred for 3 hours. The reaction mixture was diluted with DCM (125 mL), followed by addition of aqueous NaOH solution (2M, 100 mL). The mixture was stirred vigorously for 12 hours and the layers were separated. The aqueous layer was further extracted with DCM (3×50 mL). The combined extracts were washed with brine (50 mL), dried with $Na_2SO_4$, and concentrated under reduced pressure. The residue was purified with flash chromatography (Teledyne ISCO system, silica (330 g), 0-40% ethyl acetate in hexane to provide ethyl 5-(((R)-1-(2-(((S)-1-((tert-butoxycarbonyl)amino)propan-2-yl)oxy)-5-fluorophenyl)ethyl)amino)-pyrazolo[1,5-a]pyrimidine-3-carboxylate (4) (8.88 g, 60.9% yield). LC-MS m/z 502.2 (M+H)$^+$. $^1$HNMR (400 MHz, CHLOROFORM-d) δ 8.24 (s, 1H), 8.21 (d, J=7.6 Hz, 1H), 7.04 (d, J=8.4 Hz, 1H), 6.87 (d, J=6.0 Hz, 2H), 6.13 (d, J=7.2 Hz, 1H), 5.91 (br. s., 1H), 4.58 (d, J=3.6 Hz, 1H), 4.43-4.28 (m, 2H), 3.52-3.34 (m, 2H), 1.54 (d, J=6.8 Hz, 3H), 1.47-1.36 (m, 12H), 1.30 (d, J=6.4 Hz, 3H).

Step 3: Preparation of 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylic acid (5)

To a solution of ethyl 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylate (4) (6.98 g, 13.92 mmol, 1 eq.) in methanol (65 mL) and THF (20 mL) was added LiOH (2M, 47.9 mL, 95.8 mmol). The mixture was heated at 70° C. for 3 hrs, cooled to ambient temperature, and then quenched with aq. HCl (2M, 95.8 mL) to adjust pH<5. The reaction mixture was extracted with $CH_2Cl_2$ (3×50 mL), and dried over $Na_2SO_4$. After filtration, evaporation, and high vacuum dry, a white solid of 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylic acid (5) was obtained which was used in the next step without further purification. LC-MS m/z 474.2 (M+H)+.

Step 4: Preparation of 5-(((R)-1-(2-(((S)-1-aminopropan-2-yl)oxy)-5-fluorophenyl)ethyl)amino)pyrazolo[1,5-a]pyrimidine-3-carboxylic acid (6)

To a solution of 5-(((R)-1-(2-(((S)-1-((tert-butoxycarbonyl)amino)propan-2-yl)oxy)-5-fluorophenyl)ethyl)amino) pyrazolo[1,5-a]pyrimidine-3-carboxylic acid (5) (6.59 g, 13.92 mmol) in CH$_2$Cl$_2$ (130 mL) was added HCl in dioxane (4 M, 30.4 mL). Keep stirring at room temperature for 2 hours until the reaction was shown to be completed by LC-MS. The reaction mixture was concentrated, and high vacuum dried to provide compound 6 as a white solid which was used in the next step without further purification. LC-MS m/z 374.2 (M+H)+.

Step 5: Preparation of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (Compound I)

5-(((R)-1-(2-(((S)-1-aminopropan-2-yl)oxy)-5-fluorophenyl)ethyl)amino)pyrazolo[1,5-a]pyrimidine-3-carboxylic acid (6) (5.20 g, 13.93 mmol) was dissolved in DMF (75 mL) to make Solution A. To a solution of Hunig's base (DIPEA) (14.40 g, 111.4 mmol) in DMF (150 mL) and DCM (350 mL) was added solution A (25 mL) and one third of the total FDPP (5.62 g, 14.63 mmol) sequentially. The reaction was stirred for 1 hour, and LC-MS showed the completion of the coupling reaction. The same process was repeated for 2 more times. The final solution was stirred at ambient temperature for 63 hour (or until the reaction was shown to be completed by LC-MS). The reaction was quenched by addition of aqueous Na$_2$CO$_3$ solution (2M, 150 mL), and the mixture was stirred for 15 min, and extracted with DCM (3×150 mL). The combined extracts were dried with Na$_2$SO$_4$, concentrated under reduced pressure, and purified on a flash chromatography (Teledyne ISCO system, silica (220 g), 0-7.5% methanol in dichloromethane) to provide (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (Compound I) (4.38 g, 12.33 mmol, 88.5% yield) as a white solid. LC-MS: m/z [M+H]+ 356.2. $^1$H NMR (500 MHz, DMSO-d$_6$) δ ppm 9.82 (dd, J=8.02, 2.29 Hz, 1H), 8.81 (d, J=6.87 Hz, 1H), 8.58 (d, J=7.45 Hz, 1H), 8.04 (s, 1H), 7.12 (dd, J=9.45, 3.15 Hz, 1H), 6.99-7.05 (m, 1H), 6.94-6.99 (m, 1H), 6.36 (d, J=7.45 Hz, 1H), 5.53 (m, 1H), 4.45-4.52 (m, 1H), 3.90 (ddd, J=13.46, 8.31, 4.01 Hz, 1H), 3.10-3.17 (m, 1H), 1.46 (d, J=6.30 Hz, 3H), 1.44 (d, J=7.45 Hz, 3H).

Example 4: Formation of Crystalline Polymorph Form 1 of Compound I

Solid Compound I (5.55 g), obtained directly from the purification fractions of Example 3, Step 5, was re-dissolved in EA:DCM:MeOH (200:150:40), and the solution was concentrated to a volume ~70 mL to remove most of DCM and methanol. A white crystalline solid was formed. The white crystalline solid filtered to provide a crystalline polymorph form 1 of Compound I. Anal. Calcd for C18H18FN5O2: C, 60.84; H, 5.11; N, 19.71. Found: C, 60.54; H, 5.48; N, 19.88.

Large Scale Syntheses of Compound I

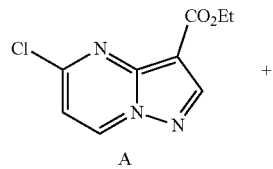

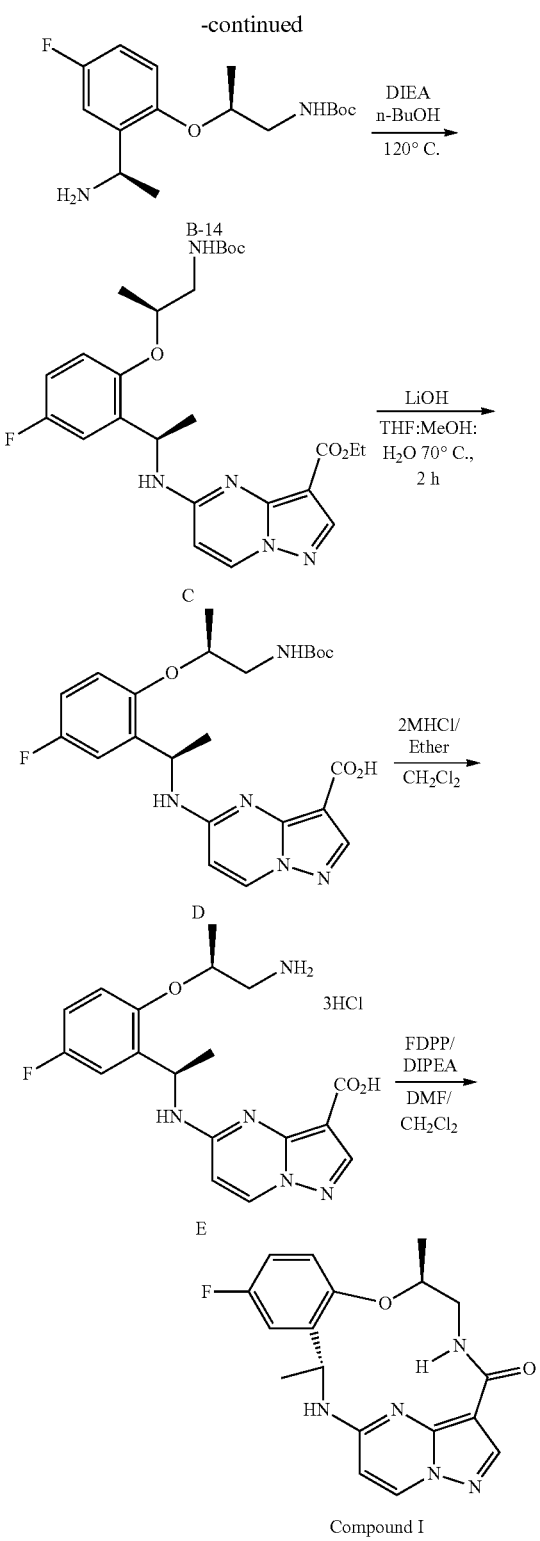

Example 5: Synthesis of Compound C

To a solution of A (126.40 g, 560.22 mmol, 1.00 eq.) and B-14 (175.00 g, 560.22 mmol, 1.00 eq.) in n-BuOH (1.70 L) was added DIEA (485.09 g, 3.75 mol, 655.53 mL, 6.70 eq.) at 25° C. The mixture was stirred at 120° C. for 5 hr. LCMS showed the starting material was completely consumed. Removed the solvent, and water (1 L) was added to the residue, and then diluted with EtOAc (1 L), extracted with EtOAc (2 L×3). The combined organic layers were washed with brine (1 L), dried over Na₂SO₄, filtered and concentrated under reduced pressure to give a residue. The residue was purified by column chromatography (SiO₂, Petroleum ether/Ethyl acetate=10/1 to 1:1) to give compound C (174.00 g, 346.92 mmol, 61.93% yield) as a white solid. LCMS: m/z 502.2 (M+H⁺). ¹H NMR (400 MHz, CHLOROFORM-d) δ 8.22 (s, 1H), 8.19 (d, J=7.6 Hz, 1H), 7.04 (d, J=8.4 Hz, 1H), 6.86 (d, J=5.2 Hz, 2H), 6.14 (d, J=6.4 Hz, 1H), 6.06 (br. s., 1H), 5.52 (br. s., 2H), 4.57 (d, J=3.2 Hz, 1H), 4.40-4.28 (m, 2H), 3.51-3.31 (m, 2H), 1.53 (d, J=6.8 Hz, 3H), 1.47-1.32 (m, 12H), 1.29 (d, J=6.0 Hz, 3H).

Example 6: Synthesis of Compound D

To a solution of 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylate (C) (140.00 g, 279.13 mmol, 1 eq.) in methanol (644 mL) and THF (252 mL) was added aqueous LiOH (3.3 M, 504 mL, 1.6632 mol, 5.95 eq.). The clear solution was heated at 70° C. for 2.5 hr. The reaction was cooled in ice bath, and then quenched with aq. HCl (3.3 M, 504 mL) to adjust pH<5. The reaction mixture was extracted with CH₂Cl₂ (1 L, and 2×500 mL). The combined extracts were washed with brine, and dried over Na₂SO₄. After filtration, evaporation, and high vacuum dry, a white solid of 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylic acid (D) was obtained (140.78 gram). The product was used in the next step without further purification.

Example 7: Synthesis of Compound E

To a solution of 5-(((R)-1-(2-(((S)-1-((tert-butoxycarbonyl)amino)propan-2-yl)oxy)-5-fluorophenyl)ethyl)amino)pyrazolo[1,5-a]pyrimidine-3-carboxylic acid (D) (132.17 g, 279.13 mmol) in CH₂Cl₂ (659 mL) was added HCl in diethyl ether (2 M, 497 mL) at ambient temperature. The reaction was stirred at ambient temperature for 22 hours, and additional HCl diethyl ether solution (2M, 100 mL) was added and stirred for 5 hours. The solid product was filtered and washed with diethyl ether, and dried in high vacuum to provide Compound E as 3'HCl salt which was used in the next step directly.

Example 8: Synthesis of Compound I from Compound E 5-(((R)-1-(2-(((S)-1-aminopropan-2-yl)oxy)-5-fluorophenyl)ethyl)amino)pyrazolo[1,5-a]pyrimidine-3-carboxylic acid (E) (208 g, 557.07 mmol) (obtained from 280 gram of C) was dissolved in DMF (1.1 L) and Hunig's Base (300 mL) to make solution A (~1700 mL). To two 4 L reaction flasks were added DMF (608 mL), DCM (3.19 L) and Hunig's Base (500 mL), respectively. To each reaction flask was added solution A (160 mL) followed by the addition of FDPP (20 g, 36.61 mmol). The reaction mixture was stirred for one hour and LCMS showed the complete consumption of compound E. The same process was repeated until all of the solution A was added to the two reaction flasks. After the last addition, additional FDPP (10 grams) was added to each flask and the final solutions were stirred at ambient temperature overnight. The reaction solution from one reaction flask was concentrated down to 1.5 L, and then diluted with DCM (4 L) and washed with aqueous Na₂CO₃ solution (2 M, 3 L). The aqueous layer was extracted with DCM (3×700 mL). The combined organic layers were washed with aqueous Na₂CO₃ solution (1 M, 2 L), water (2 L) and dried with Na₂SO₄. The same work-up procedure was applied to the second reaction flask. The combined solutions were filtered and concentrated under reduced pressure to a volume of ~600 mL. A large amount of precipitate was observed during the concentration which was stirred at 0° C. for 0.5 hr and then filtered to provide a solid product (145 grams). The filtrate was condensed to dryness and the residue was re-dissolved in DCM (1 L), and washed with aqueous HCl solution (0.4 M, 500 mL), Na₂CO₃ (2M, 1 L), water (1 L), and dried with Na₂SO₄. After filtration, the solution was concentrated to ~100 mL and the solid was precipitated out which was filtered and washed with diethyl ether (50 mL) to provide additional product (10.7 gram). The combined solid was re-dissolved in 10% methanol in DCM (2 L), and filtered to get a clear solution which was further diluted with methanol (500 mL). The solution was concentrated under reduced pressure to ~400 mL and cooled at 0° C. for 1 h. The solid was filtered and washed with cold methanol (2×60 mL) and diethyl ether (2×75 mL), and dried in high vacuum to provide (7S,13R)-11-fluoro-7,13-dimethyl-6,7,13,14-tetrahydro-1,15-ethenopyrazolo[4,3-f][1,4,8,10]-benzoxatriazacyclotridecin-4(5H)-one (Compound I) (145.302 g). The filtrate was concentrated down to ~120 mL and then cooled at 0° C. for 30 min to provide a second crop (4.815 gram). A total of 150.12 gram (75.8% yield for three steps: hydrolysis, de-boc and cyclization) of (Compound I) was obtained with a purity >98%. LC-MS: m/z [M+H]⁺ 356.2. ¹H NMR (500 MHz, DMSO-d₆) δ ppm 9.82 (dd, J=8.02, 2.29 Hz, 1H), 8.81 (d, J=6.87 Hz, 1H), 8.58 (d, J=7.45 Hz, 1H), 8.04 (s, 1H), 7.12 (dd, J=9.45, 3.15 Hz, 1H), 6.99-7.05 (m, 1H), 6.94-6.99 (m, 1H), 6.36 (d, J=7.45 Hz, 1H), 5.53 (m, 1H), 4.45-4.52 (m, 1H), 3.90 (ddd, J=13.46, 8.31, 4.01 Hz, 1H), 3.10-3.17 (m, 1H), 1.46 (d, J=6.30 Hz, 3H), 1.44 (d, J=7.45 Hz, 3H).

Synthesis of Compound A

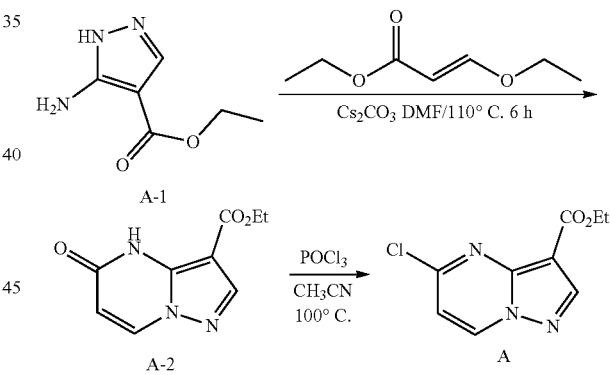

Example 9: Preparation of ethyl 5-oxo-4H-pyrazolo[1,5-a]pyrimidine-3-carboxylate (A-2)

3-Amino-1H-pyrazole-4-carboxylic acid ethyl ester (A-1) (Langchem Inc, 2.0 kg, 12.9 mol) was charged into a 50-L jacked reactor. DMF (Industrial Grade, 20 L) was then added followed by ethyl 3-ethoxyacrylate (LightChem, 3.5 kg, 24.5 mol, 1.9 eq) and Cs₂CO₃ (NuoTai Chem, 8.0 kg, 24.5 mol, 1.9 eq). The reaction mixture was heated to 110-115° C. over 40 min and agitated at this temperature overnight. IPC by LCMS showed almost all the starting materials had been consumed. The solution was then cooled to ambient temperature over 1 hr to yield a mixture. The resulting solid was collected by filtration and washed with EtOAc (6 L). The solid was collected and dissolved in water (20 L). The solution was then acidified with glacial acetic acid (6.5 L) to a pH 4. No exotherm was observed during the acidification. The resulting solid was collected by filtration and washed with water (10 L). The solid was dried at 50° C. under vacuum for 15 h to give A-2 (2.3 kg, >99.9%, 87% yield). 1H NMR (400 MHz, DMSO-$d_6$) δ 8.54 (d, J=7.91 Hz, 1H), 8.12 (s, 1H), 6.13 (d, J=7.91 Hz, 1H), 4.27 (q, J=7.11 Hz, 2H), 1.28 (t, J=7.09 Hz, 3H).

Example 10: Preparation of 5-chloropyrazolo[1,5-a]pyrimidine-3-carboxylate (A)

A-2 (2.3 kg, 11.1 mol) was charged into a 50-L jacked reactor. MeCN (Industrial Grade, 23 L) was added and cooled to 15-20° C. with agitation. Neat $POCl_3$ (8.5 kg, 55.5 mol, 5.0 eq) was added to the mixture over 10 min with no change in reactor temperature. The reaction mixture was heated to 100-105° C. over 1 hr and then agitated at this temperature for 2 hr. IPC by LCMS showed that the starting material had been consumed. The reaction solution was then transferred into a 100-L jacked reactor containing ice water (50 L, 5° C.) over 1 hr. The rate of addition was controlled so the exothermic reaction was not allowed to exceed an internal temperature of 30° C. The resulting slurry was agitated at 15-20° C. for 30 min. The solid that formed was filtered and dried at 45° C. under vacuum for 36 h to give A (1.8 kg, 99.9% pure by LCMS, 72% yield) as a white solid: 1H NMR (400 MHz, DMSO-$d_6$) δ 9.33 (d, J=7.28 Hz, 1H), 8.66 (s, 1H), 7.41 (d, J=7.15 Hz, 1H), 4.31 (q, J=7.15 Hz, 2H), 1.32 (t, J=7.09 Hz, 3H).

Synthesis of Compound B—Method A

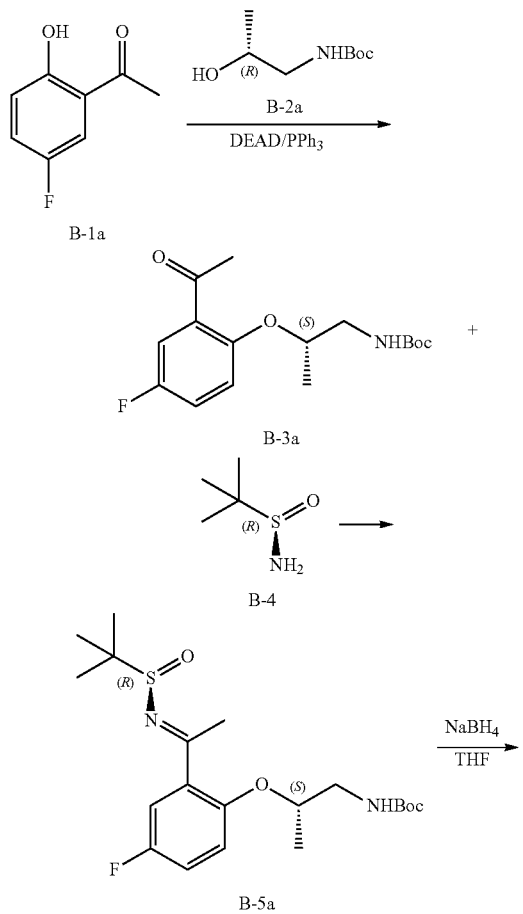

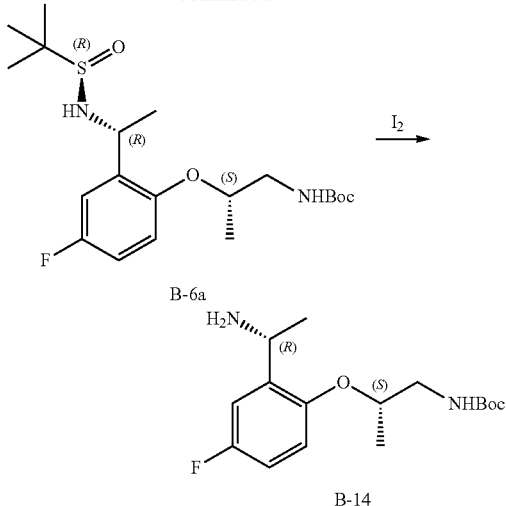

Example 11: Preparation of tert-butyl (R)-(2-hydroxypropyl)carbamate (B-2a)

To a solution of (R)-1-aminopropan-2-ol (600.00 g, 7.99 mol, 631.58 mL, 1.00 eq.) and TEA (808.33 g, 7.99 mol, 1.11 L, 1.00 eq.) in DCM (3.00 L) was added $(Boc)_2O$ (1.74 kg, 7.99 mol, 1.84 L, 1.00 eq.). The reaction mixture was stirred at 25° C. under $N_2$ for 5 hr. TLC showed the reaction was completed. The reaction mixture was partitioned between saturated $NaHCO_3$ (500 mL) and DCM (1 L) and then washed with brine (1 L). The organic layer dried over anhydrous $Na_2SO_4$ and evaporated to give compound B-2a (1.37 kg, 7.82 mol, 97.86% yield) as an oil. 1H NMR (400 MHz, CHLOROFORM-d) δ 5.00 (br. s., 1H), 3.89 (s, 1H), 3.25 (dd, J=2.8, 10.4 Hz, 1H), 3.00 (td, J=6.8, 13.6 Hz, 1H), 2.71-2.50 (m, 1H), 1.44 (s, 9H), 1.17 (d, J=6.4 Hz, 3H).

Example 12: Preparation of tert-butyl (S)-(2-(2-acetyl-4-fluorophenoxy)propyl)carbamate (B-3a)

To a solution of B-1a (500.00 g, 3.24 mol, 1.00 eq.), B-2a (851.57 g, 4.86 mol, 1.50 eq.) and $PPh_3$ (1.27 kg, 4.86 mol, 1.50 eq.) in dichloromethane (1.5 L) was added DEAD (902.79 g, 5.18 mol, 940.41 mL, 1.60 eq.) drop-wise at 0° C. The solution was stirred at 25° C. for 4 hours. TLC indicated one major new spot with larger polarity was detected, and the starting material was consumed completely. Petroleum ether (1.5 L) was added to the mixture, then filtrated the solid, the solvent of the filtrate was removed and the residue was purified by column chromatography ($SiO_2$, Petroleum ether/Ethyl acetate=20/1 to 10:1) to give B-3a (680.00 g, 2.18 mol, 67.28% yield) as a red oil. $^1$H NMR (400 MHz, CHLOROFORM-d) δ 7.38 (dd, J=3.2, 8.8 Hz, 1H), 7.13 (ddd, J=3.2, 7.2, 8.8 Hz, 1H), 6.97 (dd, J=4.0, 8.8 Hz, 1H), 5.06 (br. s., 1H), 4.63-4.52 (m, 1H), 3.52-3.39 (m, 1H), 3.38-3.27 (m, 1H), 2.59 (s, 3H), 1.42 (s, 9H), 1.32 (d, J=6.4 Hz, 3H).

Example 13: Preparation of tert-butyl ((S)-2-(2-((E)-1-(((R)-tert-butylsulfinyl)imino)-ethyl)-4-fluorophenoxy)propyl)carbamate (B-5a)

To a mixture of B-4 (219.98 g, 1.82 mol, 1.50 eq.), diglyme (162.35 g, 1.21 mol, 172.71 mL, 1.00 eq.) and B-3a (376.00 g, 1.21 mol, 1.00 eq.) in THF (1.88 L) and 2-methyltetrahydrofuran (1.88 L) was added tetraethoxytitanium (552.03 g, 2.42 mol, 501.85 mL, 2.00 eq.) in one portion at 20° C. under N₂. The mixture was stirred at 60° C. for 12 hr. TLC showed about 15% starting material remaining. The mixture was cooled to 20° C. Water (2 L) was added. The aqueous phase was extracted with ethyl acetate (2000 mL×3). The combined organic phase was washed with saturated brine (1 L), dried over anhydrous Na₂SO₄, filtered and concentrated in vacuum to give a B-5a (520.00 g, crude) as a red oil which used for the next step without further purification.

Example 14: Preparation of tert-butyl ((S)-2-(2-((R)-1-(((R)-tert-butylsulfinyl)amino)-ethyl)-4-fluorophenoxy)propyl)carbamate (B-6a)

To a solution of B-5a (520.00 g, 1.25 mol, 1.00 eq.) in THF/H₂O (3.82 L/78 mL) was added NaBH₄ (142.37 g, 3.76 mol, 3.00 eq.) at −50° C., the reaction was warmed to 25° C., and then stirred at 25° C. for 12 hr. TLC showed starting material was completely consumed. Water (1 L) was added to the mixture and extracted with EtOAc (2 L×2). The organic layer was washed with saturated NaCl (1 L) and dried over Na₂SO₄. Removed the solvent and the residue was purified by column chromatography (SiO₂, Petroleum ether/Ethyl acetate=20/1 to 10:1) to give B-6a (270.00 g, 570.40 mmol, 45.47% yield). 1H NMR (400 MHz, CHLOROFORM-d) δ 7.06 (dd, J=3.2, 9.2 Hz, 1H), 6.95 (dt, J=3.2, 8.4 Hz, 1H), 6.80 (dd, J=4.4, 9.2 Hz, 1H), 6.70 (br. s., 1H), 4.93 (d, J=6.0 Hz, 1H), 4.57-4.46 (m, 1H), 3.68-3.65 (m, 1H), 3.59-3.57 (m, 1H), 3.22-3.10 (m, 1H), 1.47 (d, J=6.8 Hz, 3H), 1.40 (s, 9H), 1.27-1.25 (m, 3H), 1.22 (s, 9H).

Example 15: Preparation of tert-butyl ((S)-2-(2-((R)-1-aminoethyl)-4-fluorophenoxy)-propyl)carbamate (B-14)

To a solution of B-6a (270.00 g, 570.40 mmol, 1.00 eq.) and molecular iodine (28.95 g, 114.08 mmol, 22.98 mL, 0.20 eq.) in THF (2.16 L) was added H₂O (540.00 mL) at 25° C. under N₂. The mixture was stirred at 50° C. for 3 hours. TLC showed the starting material was consumed completely. The mixture was concentrated to give B-14 (330.00 g, crude) as a white solid. LCMS: m/z 313.2 (M+H⁺). ¹H NMR (400 MHz, CHLOROFORM-d) δ 7.08 (dd, J=2.8, 9.4 Hz, 1H), 6.91-6.79 (m, 2H), 5.72 (br. s., 1H), 4.55-4.32 (m, 2H), 3.52-3.41 (m, 1H), 3.31-3.19 (m, 1H), 1.42 (s, 9H), 1.38 (d, J=6.8 Hz, 3H), 1.29 (d, J=6.0 Hz, 3H).

Synthesis of Compound B-14—Method B

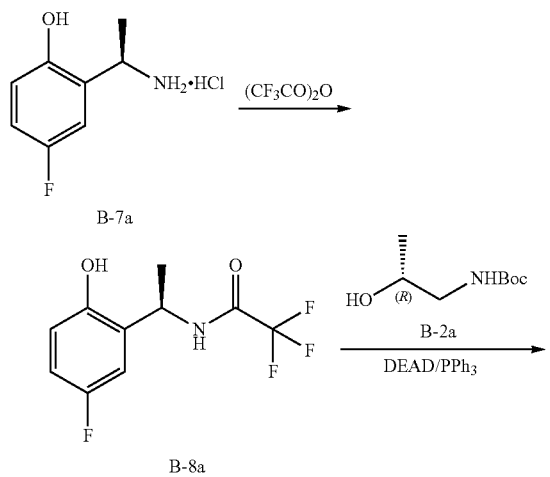

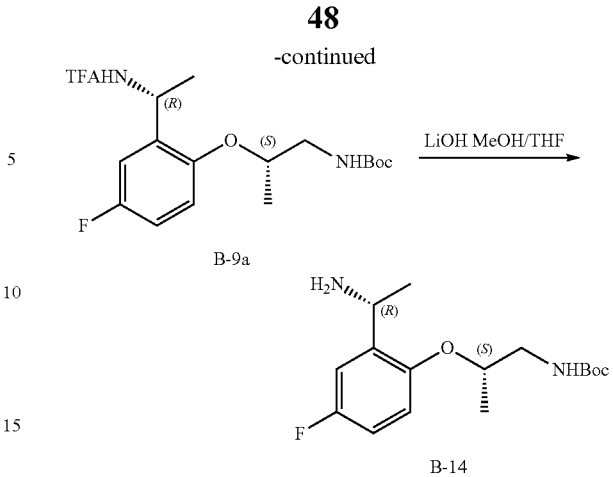

Example 16: Preparation of (R)-2,2,2-trifluoro-N-(1-(5-fluoro-2-hydroxyphenyl)-ethyl)acetamide (B-8a)

To a solution of (R)-2-(1-aminoethyl)-4-fluorophenol hydrochloride (NetChem, 1.00 g, 5.22 mmol) and triethylamine (1.58 g, 15.66 mmol) in DCM (26.10 mL) at 0° C. was added trifluoroacetic anhydride (1.26 g, 6.00 mmol) dropwise. The reaction solution was stirred for 2 hours at 0° C., and then quenched by adding to 0.5 M HCl aqueous solution (100 mL). The mixture was extracted with DCM (3×50 mL). The combined extracts were washed with 0.5 M HCl solution (2×50 mL), water (100 mL) and brine (50 mL), dried with Na₂SO₄ and concentrated under reduced pressure to provide B-8a (1.203 g, 91.5% yield). LCMS: m/z 252 (M+H⁺).

Example 17: Preparation of tert-butyl ((S)-2-(4-fluoro-2-((R)-1-(2,2,2-trifluoroacetamido)ethyl)phenoxy)propyl)carbamate (B-9a)

The mixture of (R)-2,2,2-trifluoro-N-(1-(5-fluoro-2-hydroxyphenyl)ethyl)acetamide (1.20 g, 4.78 mmol) and tert-butyl (R)-(2-hydroxypropyl)carbamate (1.68 g, 9.56 mmol) was azetrope dried together from DCM:Toluene. Then the residue was re-dissolved in DCM (2.00 mL) and PPh₃ (2.57 g, 9.80 mmol) was added to the solution. The mixture was stirred until all reactants completely dissolved. The solution was cooled to 0° C. and DIAD (1.98 g, 9.80 mmol) was added very slowly with mixing. The reaction was warmed to ambient temperature and stirred for 2 hours, and then heated to 35° C. and stirred for 16 hours. The mixture was concentrated under reduced pressure and used in the next step without purification. LCMS: m/z 431 (M+Na⁺).

Example 18: Preparation of tert-butyl ((S)-2-(2-((R)-1-aminoethyl)-4-fluorophenoxy)propyl)carbamate (B-14)

To a solution of crude tert-butyl ((S)-2-(4-fluoro-2-((R)-1-(2,2,2-trifluoroacetamido)ethyl)phenoxy)propyl)carbamate (1.95 g, 4.77 mmol) in MeOH (15 mL) and THF (5 mL) was added 2 M LiOH aqueous solution (7.03 mL). The mixture was heated at 50° C. for 6 hours, cooled to ambient temperature, and diluted with water (100 mL) and 2 M NaOH solution (25 mL), and extracted with DCM (3×75 mL). The combined extracts were washed with 2 M NaOH solution (75 mL), dried with Na₂SO₄, concentrated under reduced pressure, and dried on high vacuum. The residue was dissolved in 1:1 DCM:Hexane (100 mL), and extracted with 0.5 M HCl in 9:1 water:MeOH (3×60 mL). The combined aqueous extracts were washed with 1:3 DCM:Hexane (100 mL), neutralized with 2 M NaOH solution (100 mL), and extracted with DCM (3×100 mL). The combined DCM extracts were dried with $Na_2SO_4$, concentrated under reduced pressure, and dried on high vacuum to provide a white solid B-14 (797.6 mg, 53% yield for combined three steps). LCMS: m/z 313.2 (M+H$^+$). $^1$H NMR (400 MHz, CHLOROFORM-d) δ 7.08 (dd, J=2.8, 9.4 Hz, 1H), 6.91-6.79 (m, 2H), 5.72 (br. s., 1H), 4.55-4.32 (m, 2H), 3.52-3.41 (m, 1H), 3.31-3.19 (m, 1H), 1.42 (s, 9H), 1.38 (d, J=6.8 Hz, 3H), 1.29 (d, J=6.0 Hz, 3H).

Synthesis of Compound B-14—Method C

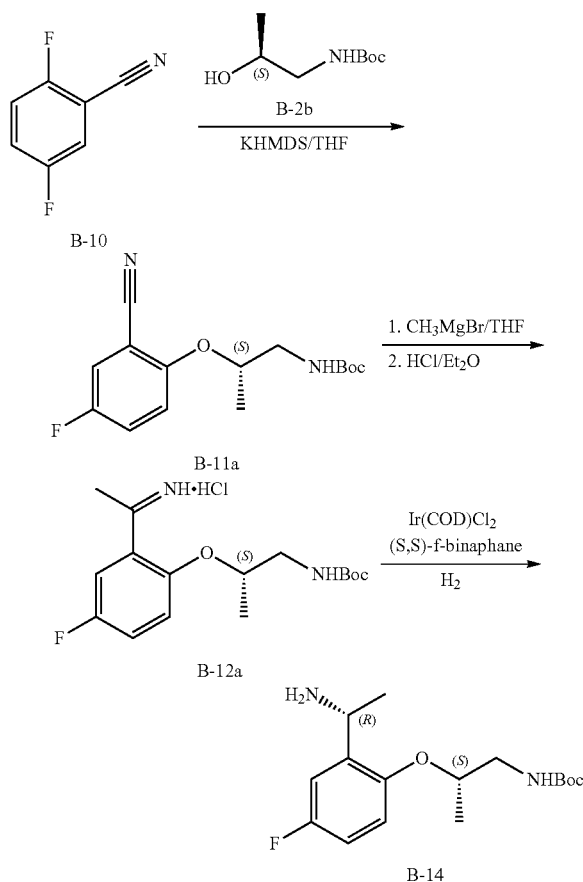

Example 19: Preparation of tert-butyl (S)-(2-(2-cyano-4-fluorophenoxy)propyl)carbamate (B-11a)

To a solution of tert-butyl (S)-(2-hydroxypropyl)carbamate (1.32 g, 7.55 mmol) and 2,5-difluorobenzonitrile (Aldrich, 1.00 g, 7.19 mmol) in THF (48 mL) at 0° C. was added KHMDS (1 M, 7.55 mL). The reaction solution was warmed to room temperature, and stirred for 18 hours under nitrogen. The solution was concentrated, diluted with DCM (150 mL), washed with 0.1 M HCl (3×150 mL), dried with $Na_2SO_4$, and concentrated under reduced pressure. Flash chromatography (ISCO system, silica (24 g), 0-25% ethyl acetate in hexane) provided B-11a (1.43 g, 4.86 mmol, 67.58% yield). LCMS: m/z 317 (M+Na$^+$). 1H NMR (500 MHz, DMSO-d$_6$) δ ppm 7.72 (dd, J=8.31, 3.15 Hz, 1H), 7.51-7.59 (m, 1H), 7.34 (dd, J=9.45, 4.30 Hz, 1H), 7.08 (t, J=5.73 Hz, 1H), 4.58 (sxt, J=5.96 Hz, 1H), 3.15-3.25 (m, 1H), 3.06-3.13 (m, 1H), 1.36 (s, 9H), 1.24 (d, J=5.73 Hz, 3H).

Example 20: Preparation of tert-butyl (S)-(2-(4-fluoro-2-(1-iminoethyl)phenoxy)propyl)-carbamate hydrochloride (B-12a)

To a solution of tert-butyl (S)-(2-(2-cyano-4-fluorophenoxy)propyl)carbamate (100.00 mg, 0.34 mmol) in THF (1.70 mL) was added MeMgBr (3 M, 0.34 mL) at −78° C. The solution was warmed to room temperature and stirred for 4 hours. The reaction was quenched with MeOH (475.20 mg, 14.83 mmol) at −78° C., then warmed to room temperature and stirred for 2 hours. The reaction solution was filtered through a celite pad, concentrated to dryness under reduced pressure, and dried on high vacuum. The residue was then re-dissolved in MTBE:DCM (1:3, 5 mL), and cooled to 0° C., followed by the addition of HCl ether solution (2 M, 0.17 mL). The reaction solution was warmed to ambient temperature and stirred for 1 hour. After concentration, the residue was suspended in MTBE (4 mL), and filtered. The solid was washed with MTBE and dried on high vacuum to afford B-12a (62.7 mg, 52.7% yield). LCMS: m/z 334 (M+Na$^+$). 1H NMR (500 MHz, DMSO-d$_6$) δ ppm 12.61 (bs, 1H), 11.70 (bs, 1H), 7.77 (dd, J=9.45, 3.15 Hz, 1H), 7.61-7.68 (m, 1H), 7.43 (dd, J=9.45, 4.30 Hz, 1H), 7.26 (t, J=5.73 Hz, 1H), 4.68-4.76 (m, 1H), 3.14-3.24 (m, 1H), 3.13-3.25 (m, 1H), 2.81 (s, 3H), 1.36 (s, 9H), 1.25 (d, J=6.30 Hz, 3H).

Example 21: Preparation of tert-butyl ((S)-2-(2-((R)-1-aminoethyl)-4-fluorophenoxy)-propyl)carbamate hydrochloride (B-14)

To a well-mixed solution of [Ir(COD)Cl]$_2$ (Strem Chemicals, 2.1 mg, 0.003 mmol) and (S, S)-f-Binaphane (Strem Chemicals, 5.1 mg, 0.006 mmol) in $CH_2Cl_2$ (1 mL) was added tert-butyl (S)-(2-(4-fluoro-2-(1-iminoethyl)phenoxy)propyl)carbamate hydrochloride (0.3 mmol) in MeOH (2 mL). The reaction vessel is then placed into a steel autoclave. The inert atmosphere is replaced by H$_2$ and the reaction mixture is stirred under 10 atmospheres H$_2$ (150 psi) at ambient temperature for 12 hr. The resulting mixture is concentrated under vacuum and dissolved in saturated aqueous NaHCO$_3$ (5 mL). After stirring for 10 min, the mixture is extracted with $CH_2Cl_2$ (3×2 mL), dried over $Na_2SO_4$, concentrated, and dried under high vacuum to provide compound B-14. $^1$H NMR (400 MHz, CHLOROFORM-d) δ 7.08 (dd, J=2.8, 9.4 Hz, 1H), 6.91-6.79 (m, 2H), 5.72 (br. s., 1H), 4.55-4.32 (m, 2H), 3.52-3.41 (m, 1H), 3.31-3.19 (m, 1H), 1.42 (s, 9H), 1.38 (d, J=6.8 Hz, 3H), 1.29 (d, J=6.0 Hz, 3H).

Synthesis of Compound B-14—Method D

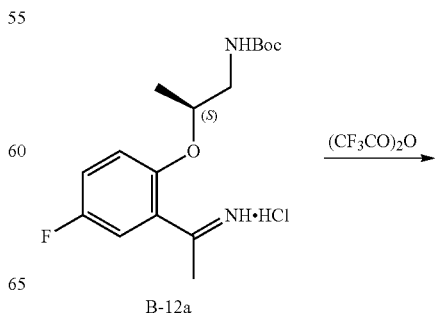

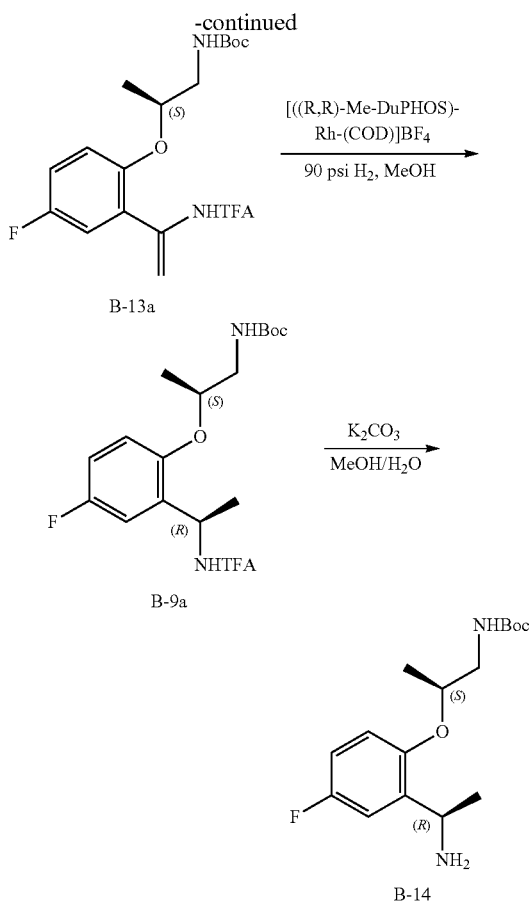

Example 22: Preparation of tert-butyl (S)-(2-(4-fluoro-2-(1-(2,2,2-trifluoroacetamido)-vinyl)phenoxy)propyl)carbamate (B-13a)

To a solution of tert-butyl (S)-(2-(4-fluoro-2-(1-iminoethyl)phenoxy)propyl)carbamate hydrochloride (25.00 mg, 0.072 mmol) and trifluoroacetic anhydride (17.41 mg, 0.083 mmol) in DCM (0.36 mL) at 0° C. was added triethylamine (43.76 mg, 0.432 mmol). The reaction solution was stirred for 3 hours at 0° C., quenched with addition of 0.5 M aqueous HCl (25 mL), extracted with DCM (150 mL). The extract was washed with 0.5 M aqueous HCl (25 mL), dried with Na$_2$SO$_4$, and concentrated under reduced pressure. Flash chromatography (ISCO system, silica (12 g), 0-50% ethyl acetate in hexane) provided B-13a (15.70 mg, 0.038 mmol, 53.60% yield). LCMS: m/z 429 (M+Na$^+$). 1H NMR (500 MHz, DMSO-d6) δ ppm 10.70 (s, 1H) 7.13-7.22 (m, 1H) 7.06-7.13 (m, 2H) 6.92 (t, J=6.01 Hz, 1H) 5.66 (s, 1H) 5.18 (s, 1H) 4.42 (q, J=6.30 Hz, 1H) 3.17 (dt, J=13.75, 6.01 Hz, 1H) 2.91-3.01 (m, 1H) 1.35 (s, 9H) 1.13 (d, J=6.30 Hz, 3H).

Example 23: Preparation of tert-butyl ((S)-2-(4-fluoro-2-((R)-1-(2,2,2-trifluoroacetamido)ethyl)phenoxy)propyl)carbamate (B-9a)

tert-butyl (S)-2-(4-fluoro-2-(1-(2,2,2-trifluoroacetamido)vinyl)phenoxy)propyl)carbamate (3.00 mmol) and [((R,R)-Me-DuPHOS)—Rh—(COD)]BF$_4$ (Strem Chemicals, 0.2 mol %) is placed in a glass pressure vessel, which was then purged with hydrogen for three times. Degassed methanol (10 mL) was then added and the vessel further is purged with hydrogen and charged to 90 psi hydrogen. After stirring for 20 hr the reaction mixture is evaporated to afford a residue. This residue was dissolved in EtOAc (5 mL) and the solution was filtered through a short silica plug to remove catalyst residues. The solvent is then evaporated to afford compound B-9a.

Example 24: Preparation of tert-butyl ((S)-2-(2-((R)-1-aminoethyl)-4-fluorophenoxy)propyl)carbamate hydrochloride (B-14)

To a solution of tert-butyl ((S)-2-(4-fluoro-2-((R)-1-(2,2,2-trifluoroacetamido)ethyl)-phenoxy)propyl)carbamate (1.00 mmol) in methanol (30 mL) and water (10 mL) was added K$_2$CO$_3$ (3.00 mmol). The mixture is heated at 60° C. until the hydrolysis was complete. The reaction mixture was extracted three times with dichloromethane (30 mL). The combined extracts are dried over Na$_2$SO$_4$, filtered, concentrated, and dried under high vacuum to afford compound B-14. $^1$H NMR (400 MHz, CHLOROFORM-d) δ 7.08 (dd, J=2.8, 9.4 Hz, 1H), 6.91-6.79 (m, 2H), 5.72 (br. s., 1H), 4.55-4.32 (m, 2H), 3.52-3.41 (m, 1H), 3.31-3.19 (m, 1H), 1.42 (s, 9H), 1.38 (d, J=6.8 Hz, 3H), 1.29 (d, J=6.0 Hz, 3H).

Testing of Crystalline Polymorph Form 1 of Compound I

Example 25: Powder X-ray Diffraction (PXRD) of crystalline polymorph form 1 of Compound I A sample of Compound I, crystalline polymorph form 1, was run for PXRD on a Bruker D8 Advance equipped with a 1-D Lynxeye silicon strip detector and Cu radiation (1.54178 Å). The sample was spun during collection to limit preferred orientation peaks. Data was collected from 2°-50° 2θ using a step size of 0.02° and scan rate of 0.25 s per step. Results are shown in FIG. 1.

Example 26: Differential Scanning Calorimetry (DSC) of Crystalline Polymorph Form 1 of Compound I DSC measurements were carried out using a Seiko Model SSC/5200 Differential Scanning Calorimeter. A 7.16 mg sample of Compound I, crystalline polymorph form 1, was equilibrated at 30° C., and then ramped to 380° C. at a rate of 10° C./min. The sample of Compound I, crystalline polymorph form 1, showed a melting point of 345.5° C. Results are shown in FIG. 2.

BIOLOGICAL EXAMPLES

Example 27: Kinase Binding Assays

Kinase binding assays were performed at DiscoveRx using the general KINOMEscan K$_d$ Protocol (Fabian, M. A. et al., "A small molecule-kinase interaction map for clinical kinase inhibitors," Nat. Biotechnol. 2005, 23(3):329-36). For most assays, kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR. With this method, Compound I had a binding affinity with JAK2 of $K_d$=0.082 nM and ALK of $K_d$=5.7 nM.

Example 28: EML4-ALK Ba/F3 Stable Cell Line Creation and Cell Proliferation Assay The EML4-ALK wild-type gene (variant 1) was synthesized at GenScript and cloned into pCDH-CMV-MCS-EF1-Puro plasmid (System Biosciences, Inc). Ba/F3-EML4-ALK wild type cell line was generated by infecting Ba/F3 cells with lentivirus containing EML4-ALK wide-type. Stable cell lines were selected by puromycin treatment, followed by IL-3 withdrawal. 5000 cells were seeded in 384 well white plate overnight before compound treatment. Cell proliferation was measured using CellTiter-Glo luciferase-based ATP detection assay (Promega) following the manufactures's protocol after 48 hours of various concentration of compound incubation. $IC_{50}$ determinations were performed using GraphPad Prism software (GraphPad, Inc., San Diego, Calif.). Data for Compound I is presented in Table 2.

Example 29: Cell Proliferation Assays

Colorectal cell lines KM 12 (harboring endogenous TPM3-TRKA fusion gene) cells were cultured in DMEM medium, supplemented with 10% fetal bovine serum and 100 U/mL of penicillin/streptomycin. 5000 cells were seeded in 384 well white plate for 24 hours before compounds treatment. Cell proliferation was measured using CellTiter-Glo luciferase-based ATP detection assay (Promega) following the manufactures's protocol after 72 hours incubation. $IC_{50}$ determinations were performed using GraphPad Prism software (GraphPad, Inc., San Diego, Calif.).

Colorectal cell line KM12 (harboring endogenous TPM3-TRKA fusion gene) cells were cultured in DMEM medium, supplemented with 10% fetal bovine serum and 100 U/mL of penicillin/streptomycin. Essential thrombocythemia cell line SET-2 cells (harboring endogenous JAK2 V618F point mutation) or T cell lymphoma Karpas-299 cell line (harboring endogenous NPM-ALK fusion gene) were cultured in RPMI medium, supplemented with 10% fetal bovine serum and 100 U/mL of penicillin/streptomycin. 5000 cells were seeded in 384 well white plate for 24 hours before compounds treatment. Cell proliferation was measured using CellTiter-Glo luciferase-based ATP detection assay (Promega) following the manufactures's protocol after 72 hours incubation. $IC_{50}$ determinations were performed using GraphPad Prism software (GraphPad, Inc., San Diego, Calif.).

Data for Compound I is presented in Table 2.

TABLE 2

| KM 12 cell prolif. $IC_{50}$ (nM) | SET2 cell proli. $IC_{50}$ (nM) | Karpas 299 cell proli. $IC_{50}$ (nM) | EML4-ALK Ba/F3 cell proli. $IC_{50}$ (nM) |
|---|---|---|---|
| 0.5 | 242 | 23.7 | 21.1 |

What is claimed is:

1. A crystalline polymorph form of (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one, wherein the crystalline polymorph form has a powder X-ray diffraction pattern comprising a peak at diffraction angle (2θ) of 27.4±0.1.

2. The crystalline polymorph form of claim 1, wherein the crystalline polymorph form has a powder X-ray diffraction pattern comprising peaks at diffraction angles (2θ) of 9.4±0.1, 16.1±0.1, 16.5±0.1, 18.8±0.1, 21.2±0.1, 22.8±0.1, and 27.4±0.1.

3. The crystalline polymorph form of claim 1, wherein the crystalline polymorph form has a powder X-ray diffraction pattern comprising peaks at diffraction angles (2θ) of 27.4±0.1 and 22.8±0.1.

4. The crystalline polymorph form of claim 1, wherein the crystalline polymorph form has a powder X-ray diffraction pattern comprising peaks at diffraction angles (2θ) of 27.4±0.1 and 21.2±0.1.

5. The crystalline polymorph form of claim 1, wherein the crystalline polymorph form has a powder X-ray diffraction pattern comprising peaks at diffraction angles (2θ) of 27.4±0.1 and 18.8±0.1.

6. The crystalline polymorph form of claim 1, wherein the crystalline polymorph form has a powder X-ray diffraction pattern comprising peaks at diffraction angles (2θ) of 27.4±0.1 and 16.5±0.1.

7. The crystalline polymorph form of claim 1, wherein the crystalline polymorph form has a powder X-ray diffraction pattern comprising peaks at diffraction angles (2θ) of 27.4±0.1 and 16.1±0.1.

8. The crystalline polymorph form of claim 1, wherein the crystalline polymorph form has a powder X-ray diffraction pattern comprising peaks at diffraction angles (2θ) of 27.4±0.1 and 9.4±0.1.

9. The crystalline polymorph form of claim 1, wherein the crystalline polymorph form has a powder X-ray diffraction pattern comprising peaks at diffraction angles (2θ) of 27.4±0.1, 22.8±0.1, and 21.2±0.1.

10. The crystalline polymorph form of claim 1, wherein the crystalline polymorph form has a powder X-ray diffraction pattern comprising peaks at diffraction angles (2θ) of 27.4±0.1, 22.8±0.1, and 18.8±0.1.

11. The crystalline polymorph form of claim 1, wherein the crystalline polymorph form has a powder X-ray diffraction pattern comprising peaks at diffraction angles (2θ) of 27.4±0.1, 22.8±0.1, and 16.5±0.1.

12. The crystalline polymorph form of claim 1, wherein the crystalline polymorph form has a powder X-ray diffraction pattern comprising peaks at diffraction angles (2θ) of 27.4±0.1, 22.8±0.1, and 16.1±0.1.

13. The crystalline polymorph form of claim 1, wherein the crystalline polymorph form has a powder X-ray diffraction pattern comprising peaks at diffraction angles (2θ) of 27.4±0.1, 22.8±0.1, and 9.4±0.1.

14. The crystalline polymorph form of claim 1, wherein the crystalline polymorph form has a powder X-ray diffraction pattern comprising peaks at diffraction angles (2θ) of 27.4±0.1, 21.2±0.1, and 18.8±0.1.

15. The crystalline polymorph form of claim 1, wherein the crystalline polymorph form has a powder X-ray diffraction pattern comprising peaks at diffraction angles (2θ) of 27.4±0.1, 21.2±0.1, and 16.5±0.1.

16. The crystalline polymorph form of claim 1, wherein the crystalline polymorph form has a powder X-ray diffraction pattern comprising peaks at diffraction angles (2θ) of 27.4±0.1, 21.2±0.1, and 16.1±0.1.

17. The crystalline polymorph form of claim 1, wherein the crystalline polymorph form has a powder X-ray diffraction pattern comprising peaks at diffraction angles (2θ) of 27.4±0.1, 21.2±0.1, and 9.4±0.1.

18. The crystalline polymorph form of claim 1, wherein the crystalline polymorph form has a powder X-ray diffraction pattern comprising peaks at diffraction angles (2θ) of 27.4±0.1, 18.8±0.1, and 16.5±0.1.

19. The crystalline polymorph form of claim 1, wherein the crystalline polymorph form has a powder X-ray diffraction pattern comprising peaks at diffraction angles (2θ) of 27.4±0.1, 18.8±0.1, and 16.1±0.1.

20. The crystalline polymorph form of claim 1, wherein the crystalline polymorph form has a powder X-ray diffraction pattern comprising peaks at diffraction angles (2θ) of 27.4±0.1, 18.8±0.1, and 9.4±0.1.

* * * * *